United States Patent
Stafford et al.

(10) Patent No.: US 10,731,148 B2
(45) Date of Patent: Aug. 4, 2020

(54) USE OF LAMBDA-GAM PROTEIN IN RIBOSOMAL DISPLAY TECHNOLOGY

(71) Applicant: SUTRO BIOPHARMA, INC., South San Francisco, CA (US)

(72) Inventors: Ryan Stafford, Foster City, CA (US); Christopher D. Thanos, Tiburon, CA (US)

(73) Assignee: SUTRO BIOPHARMA, INC., South San Francisco, CA (US)

(*) Notice: Subject to any disclaimer, the term of this patent is extended or adjusted under 35 U.S.C. 154(b) by 0 days.

(21) Appl. No.: 15/867,471

(22) Filed: Jan. 10, 2018

(65) Prior Publication Data

US 2018/0142232 A1 May 24, 2018

Related U.S. Application Data

(62) Division of application No. 14/786,147, filed as application No. PCT/US2014/035325 on Apr. 24, 2014, now Pat. No. 9,896,685.

(60) Provisional application No. 61/815,951, filed on Apr. 25, 2013.

(51) Int. Cl.
*C40B 40/10* (2006.01)
*C12N 15/10* (2006.01)
*C40B 50/06* (2006.01)

(52) U.S. Cl.
CPC .......... *C12N 15/1041* (2013.01); *C40B 40/10* (2013.01); *C40B 50/06* (2013.01)

(58) Field of Classification Search
None
See application file for complete search history.

(56) References Cited

U.S. PATENT DOCUMENTS

| 5,922,545 | A | 7/1999 | Mattheakis et al. |
| 9,896,685 | B2 | 2/2018 | Stafford et al. |
| 2006/0177862 | A1 | 8/2006 | Osbourn et al. |
| 2006/0246515 | A1 | 11/2006 | Zhu et al. |
| 2008/0214406 | A1 | 9/2008 | Crea |
| 2008/0275219 | A1 | 11/2008 | Green et al. |
| 2012/0058906 | A1 | 3/2012 | Smider et al. |
| 2014/0030273 | A1 | 1/2014 | Verploegen et al. |

(Continued)

FOREIGN PATENT DOCUMENTS

| EP | 2647704 A1 | 10/2013 |
| EP | 2657334 A1 | 10/2013 |

(Continued)

OTHER PUBLICATIONS

Court et al., "The Crystal Structure of λ-Gam Protein Suggest a Model for RecBCD Inhibition" *J. Mol. Biol.* 371:25-33 (2007).

(Continued)

*Primary Examiner* — Christian C Boesen
(74) *Attorney, Agent, or Firm* — Kilpatrick Townsend & Stockton LLP

(57) ABSTRACT

Methods and systems for increasing the stability of a nucleic acid template that encodes a protein of interest in a cell free translation system or a ribosomal display reaction system are described. In some embodiments, the nucleic acid template is an RNA or mRNA. The stability of the RNA template is increased by adding the bacteriophage lambda protein Gam to the cell free extract used in the translation system. The addition of Gam protein increases the longevity of the reaction system, thereby increasing the efficiency of the ribosomal display reaction system.

6 Claims, 4 Drawing Sheets

Specification includes a Sequence Listing.

(56) References Cited

U.S. PATENT DOCUMENTS

2016/0060620 A1 3/2016 Stafford et al.
2016/0069897 A1 3/2016 Stafford et al.

FOREIGN PATENT DOCUMENTS

| EP | 2989202 | 3/2016 |
|---|---|---|
| EP | 2989239 A4 | 3/2016 |
| EP | 2989239 | 11/2016 |
| EP | 2989239 B1 | 7/2018 |
| WO | 02072890 A1 | 9/2002 |
| WO | 2014176327 A2 | 10/2014 |
| WO | 2014176439 A1 | 10/2014 |
| WO | 2014176327 A3 | 12/2014 |

OTHER PUBLICATIONS

EP14788445.6, "Extended European Search Report", dated Oct. 14, 2016, 8 pages.
Friedman et al., "Selective inhibition of *Escherichia coli* RecBC activities by plasmid-encoded GamS function of phage lambda", *Gene* 34:255-263 (1986).
Hara et al., "Stabilized Ribosome Display for In Vitro Selection", *Methods in Molecular Biology*,805(1):59-73 (Jan. 1, 2012) ,
He et al., "Ribosome display: Cell-free protein display technology", *Briefings in Functional Genomics and Proteomics*, 1(2):204-212 (Jul. 2002)
Jiang et al., Expression of Fab fragment of catalytic antibody 6D9 in an *Escherichia coli* in vitro coupled transcription/translation system, FEBS Letters 514, 2002, pp. 290-294.
Kojoh et al., In vitro affinity maturation based on Ribosome Display System with PUREfrex, URL:http://www.genefrontier.com/wps/wp-content/uploads/2012/05/PEGS2012_posterl.pdf, Jan. 1, 2012, 1 page.
PCT/US2014/035130 , "International Preliminary Report on Patentability", dated Nov. 5, 2015, 10 pages.
PCT/US2014/035130 , "International Search Report and Written Opinion", dated Oct. 24, 2014, 13 pages.
PCT/US2014/035325 , "International Preliminary Report on Patentability", dated Nov. 5, 2015, 9 pages.
PCT/US2014/035325 , "International Search Report and Written Opinion", dated Aug. 13, 2014, 14 pages.
Sawata et al., "A system based on specific protein-RNA interactions for analysis of target protein-protein interactions in vitro: successful selection of membrance-bound Bak-Bcl-xL proteins in vitro", *Protein Engineering, Design & Selection*, 17(6):501-508 (Aug. 3, 2004).
Sawata et al., "Development of an advanced polysome display system dependant on a specific protein-RNA motif interaction", Nucleic Acids Research, 1(1):99-100 (Nov. 1, 2001).
Schaffitzel et al., "Ribosome display: an in vitro method for selection and evolution of antibodies from libraries", *Journal of Immunological Methods*, 231:119-135 (1999).
Stafford et al., "In vitro Fab display: a cell-free system for IgG discovery", Protein Engineering Design and Selection, vol. 27, No. 4,, Feb. 28, 2014, pp. 97-109.
Villemagne et al., "Highly efficient ribosome display selection by use of purified components for in vitro translation", *Journal of Immunological Methods*, 313:140-148 (2006).
Wada et al., "Ribosome Display Selection of a Metal-Binding Motif From an Artificial Peptide Library", *Biotechnology & Bioengineering*, 101(5):1102-1107 (Dec. 1, 2008).
Whittaker , "Cell-free protein synthesis: the state of the art", Biotechnol Lett., 35(2), Feb. 2013, pp. 1-15.
U.S. Appl. No. 14/786,147, filed Oct. 21, 2015.
PCT/US2014/035325, filed Apr. 24, 2014.
Feige et al., "How Antibodies Fold," *Trends in Biochemical Sciences*, Apr. 2010, 35(4):189-198.
Kindt et al., "Immunology," New York: W. H. Freeman and Company, 2007, Ed. 6, ISBN: 978-0-7167-8590-3, 4 pages.
Kojoh Declaration and Exhibits KK1-KK4, Apr. 2, 2019, 19 pages.
Lou et al., "Affinity Maturation by Chain Shuffling and Site Directed Mutagenesis," Kontermann, R. And Dubel, S. eds., *Antibody Engineering*, Springer-Verlag, Berlin, 2010, 16 pages.
Odegrip et al., "CIS display: *In vitro* selection of peptides from libraries of protein-DNA complexes" Proc. Natl. Acad. Sci. USA, Jan. 12, 2004, 101(9):2806-2810.
Roberts et al., "RNA-peptide fusions for the *in vitro* selection of peptides and proteins," Proc. Natl. Acad. Sci. USA, Nov. 1997, 94:12297-12302.
Stafford et al., "*In vitro* Fab display: a cell-free system for IgG discovery," Protein Engineering, Design & Selection, Feb. 28, 2014, 27(4):97-109.
Wikipedia, "Creatin kinase" Mar. 23, 2013, 6 pages.
Wikipedia, "mRNA display," Mar. 16, 2013, [cited Mar. 28, 2019], Available from: [https://en.wikipedia.org/w/index.php?title=MRNA_display&oldid=544583367].
Wilson, Ian et al., "Antibody-antigen interactions," Current Opinion in Structural Biology, 1993, 3:113-118.
Yin et al., "Aglycosylated antibodies and antibody fragments produced in a scalable in vitro transcription-translation system," mAbs, Mar./Apr. 2012, 4(2):217-225.
EP14788445.6 , "Notice of Opposition," dated Apr. 23, 2019, 1 page.
EP14788445.6 , "Communication of Notice of Opposition," dated Apr. 11, 2019, 7 pages.
EP13165182, "European Search Report," dated Jul. 10, 2013, 5 pages.
Proprietor's letter of May 11, 2017 in response to the European search opinion of Oct. 14, 2016, including annex, 6 pages.
EP14788445.6 , "Summons to Attend Oral Proceedings", dated Oct. 7, 2019, 8 pages.

SEQUENCE LISTING

<160> NUMBER OF SEQ ID NOS: 52

<210> SEQ ID NO 1
<211> LENGTH: 98
<212> TYPE: PRT
<213> ORGANISM: Escherichia coli
<220> FEATURE:
<223> OTHER INFORMATION: E. coli strain K-12 substrain BW2952 host-nuclease inhibitor protein gam, GAM, lambda GamS

<400> SEQUENCE: 1

Met Asn Ala Tyr Tyr Ile Gln Asp Arg Leu Glu Ala Gln Ser Trp Ala
1               5                   10                  15

Arg His Tyr Gln Gln Leu Ala Arg Glu Glu Lys Glu Ala Glu Leu Ala

```
                    20                  25                  30

Asp Asp Met Glu Lys Gly Ile Pro Gln His Leu Phe Glu Ser Leu Cys
            35                  40                  45

Ile Asp His Leu Gln Arg His Gly Ala Ser Lys Lys Ser Ile Thr Arg
        50                  55                  60

Ala Phe Asp Asp Asp Val Glu Phe Gln Glu Arg Met Ala Glu His Ile
65                  70                  75                  80

Arg Tyr Met Val Glu Thr Ile Ala His His Gln Val Asp Ile Asp Ser
                85                  90                  95

Glu Val

<210> SEQ ID NO 2
<211> LENGTH: 324
<212> TYPE: DNA
<213> ORGANISM: Artificial Sequence
<220> FEATURE:
<223> OTHER INFORMATION: synthetic E. coli strain K-12 substrain BW2952
      host-nuclease inhibitor protein gam, GAM, lambda
      GamS with His tag, GamSHis gene

<400> SEQUENCE: 2
atgaacgctt attacattca ggatcgtctt gaggctcaga gctgggcgcg tcactaccag      60
cagctcgccc gtgaagagaa agaggcagaa ctggcagacg acatggaaaa agggatcccc    120
cagcacctgt ttgaatcgct atgcatcgat catttgcaac gccacggggc cagcaaaaaa    180
tccattaccc gtgcgtttga tgacgatgtt gagtttcagg agcgcatggc agaacacatc    240
cggtacatgg ttgaaaccat tgctcaccac caggttgata ttgattcaga ggtaggggggt    300 tctcatcatc atcatcatca ttaa                                           324

<210> SEQ ID NO 3
<211> LENGTH: 107
<212> TYPE: PRT
<213> ORGANISM: Artificial Sequence
<220> FEATURE:
<223> OTHER INFORMATION: synthetic E. coli strain K-12 substrain BW2952
      host-nuclease inhibitor protein gam, GAM, lambda
      GamS with His tag, GamSHis protein

<400> SEQUENCE: 3

Met Asn Ala Tyr Tyr Ile Gln Asp Arg Leu Glu Ala Gln Ser Trp Ala
1               5                   10                  15

Arg His Tyr Gln Gln Leu Ala Arg Glu Glu Lys Glu Ala Glu Leu Ala
            20                  25                  30

Asp Asp Met Glu Lys Gly Ile Pro Gln His Leu Phe Glu Ser Leu Cys
        35                  40                  45

Ile Asp His Leu Gln Arg His Gly Ala Ser Lys Lys Ser Ile Thr Arg
    50                  55                  60

Ala Phe Asp Asp Asp Val Glu Phe Gln Glu Arg Met Ala Glu His Ile
65                  70                  75                  80

Arg Tyr Met Val Glu Thr Ile Ala His His Gln Val Asp Ile Asp Ser
                85                  90                  95

Glu Val Gly Gly Ser His His His His His
            100                 105

<210> SEQ ID NO 4
<211> LENGTH: 56
<212> TYPE: DNA
<213> ORGANISM: Artificial Sequence
<220> FEATURE:
```

<223> OTHER INFORMATION: synthetic primer H1a For for Fab HC library
      construction

<400> SEQUENCE: 4
cgcggcaagc ggttttaaca ttavtrrtwm ykmtatccac tgggtgcgtc aagcac       56

<210> SEQ ID NO 5
<211> LENGTH: 56
<212> TYPE: DNA
<213> ORGANISM: Artificial Sequence
<220> FEATURE:
<223> OTHER INFORMATION: synthetic primer H1a Rev for Fab HC library
      construction

<400> SEQUENCE: 5
gtgcttgacg cacccagtgg atakmrkway yabtaatgtt aaaaccgctt gccgcg       56

<210> SEQ ID NO 6
<211> LENGTH: 56
<212> TYPE: DNA
<213> ORGANISM: Artificial Sequence
<220> FEATURE:
<223> OTHER INFORMATION: synthetic primer H1bFor for Fab HC library
      construction

<400> SEQUENCE: 6
cgcggcaagc ggttttaaca ttavtrrtwm ykggatccac tgggtgcgtc aagcac       56

<210> SEQ ID NO 7
<211> LENGTH: 56
<212> TYPE: DNA
<213> ORGANISM: Artificial Sequence
<220> FEATURE:
<223> OTHER INFORMATION: synthetic primer H1b Rev for Fab HC library
      construction

<400> SEQUENCE: 7
gtgcttgacg cacccagtgg atccmrkway yabtaatgtt aaaaccgctt gccgcg       56

<210> SEQ ID NO 8
<211> LENGTH: 77
<212> TYPE: DNA
<213> ORGANISM: Artificial Sequence
<220> FEATURE:
<223> OTHER INFORMATION: synthetic primer H2a For for Fab HC library
      construction

<400> SEQUENCE: 8
gggtaagggc ctggaatggg ttgstdggat tdmtccgdmt rrcggtdmta ccdactatgc   60
ggatagcgtg aaaggcc                                                  77

<210> SEQ ID NO 9
<211> LENGTH: 77
<212> TYPE: DNA
<213> ORGANISM: Artificial Sequence
<220> FEATURE:
<223> OTHER INFORMATION: synthetic primer H2a Rev for Fab HC library
      construction

<400> SEQUENCE: 9
ggcctttcac gctatccgca tagthggtak haccgyyakh cggakhaatc chascaaccc   60
attccaggcc cttaccc                                                  77

<210> SEQ ID NO 10
<211> LENGTH: 77

```
<212> TYPE: DNA
<213> ORGANISM: Artificial Sequence
<220> FEATURE:
<223> OTHER INFORMATION: synthetic primer H2b For for Fab HC library
      construction

<400> SEQUENCE: 10
gggtaagggc ctggaatggg ttgstdhtat tdmtccgdmt rrcggtdmta ccdactatgc    60
ggatagcgtg aaaggcc                                                  77

<210> SEQ ID NO 11
<211> LENGTH: 77
<212> TYPE: DNA
<213> ORGANISM: Artificial Sequence
<220> FEATURE:
<223> OTHER INFORMATION: synthetic primer H2b Rev for Fab HC library
      construction

<400> SEQUENCE: 11
ggcctttcac gctatccgca tagthggtak haccgyyakh cggakhaata dhascaaccc    60
attccaggcc cttaccc                                                  77

<210> SEQ ID NO 12
<211> LENGTH: 77
<212> TYPE: DNA
<213> ORGANISM: Artificial Sequence
<220> FEATURE:
<223> OTHER INFORMATION: synthetic primer H2c For for Fab HC library
      construction

<400> SEQUENCE: 12
gggtaagggc ctggaatggg ttgstgaaat tdmtccgdmt rrcggtdmta ccdactatgc    60
ggatagcgtg aaaggcc                                                  77

<210> SEQ ID NO 13
<211> LENGTH: 77
<212> TYPE: DNA
<213> ORGANISM: Artificial Sequence
<220> FEATURE:
<223> OTHER INFORMATION: synthetic primer H2c Rev for Fab HC library
      construction

<400> SEQUENCE: 13
ggcctttcac gctatccgca tagthggtak haccgyyakh cggakhaatt tcascaaccc    60
attccaggcc cttaccc                                                  77

<210> SEQ ID NO 14
<211> LENGTH: 80
<212> TYPE: DNA
<213> ORGANISM: Artificial Sequence
<220> FEATURE:
<223> OTHER INFORMATION: synthetic primer H3a For for Fab HC library
      construction
<220> FEATURE:
<221> NAME/KEY: modified_base
<222> LOCATION: (1)...(80)
<223> OTHER INFORMATION: n = g, a, c or t

<400> SEQUENCE: 14
gcagaggaca ctgccgtcta ctattgtgcg cgcnnknnkn nknnknnknn knnknnkatg    60
gactactggg gccagggtac                                               80

<210> SEQ ID NO 15
<211> LENGTH: 80
```

```
<212> TYPE: DNA
<213> ORGANISM: Artificial Sequence
<220> FEATURE:
<223> OTHER INFORMATION: synthetic primer H3a Rev for Fab HC library
      construction
<220> FEATURE:
<221> NAME/KEY: modified_base
<222> LOCATION: (1)...(80)
<223> OTHER INFORMATION: n = g, a, c or t

<400> SEQUENCE: 15
gtaccctggc cccagtagtc catmnnmnnm nnmnnmnnmn nmnnmnngcg cgcacaatag    60
tagacggcag tgtcctctgc                                               80

<210> SEQ ID NO 16
<211> LENGTH: 82
<212> TYPE: DNA
<213> ORGANISM: Artificial Sequence
<220> FEATURE:
<223> OTHER INFORMATION: synthetic primer H3b For for Fab HC library
      construction
<220> FEATURE:
<221> NAME/KEY: modified_base
<222> LOCATION: (1)...(82)
<223> OTHER INFORMATION: n = g, a, c or t

<400> SEQUENCE: 16
gcagaggaca ctgccgtcta ctattgtgcg cgcnnknnkn nknnknnknn knnknnkttt    60
gactactggg gccagggtac gc                                            82

<210> SEQ ID NO 17
<211> LENGTH: 82
<212> TYPE: DNA
<213> ORGANISM: Artificial Sequence
<220> FEATURE:
<223> OTHER INFORMATION: synthetic primer H3b Rev for Fab HC library
      construction
<220> FEATURE:
<221> NAME/KEY: modified_base
<222> LOCATION: (1)...(82)
<223> OTHER INFORMATION: n = g, a, c or t

<400> SEQUENCE: 17
gcgtaccctg gccccagtag tcaaamnnmn nmnnmnnmnn mnnmnnmnng cgcgcacaat    60
agtagacggc agtgtcctct gc                                            82

<210> SEQ ID NO 18
<211> LENGTH: 29
<212> TYPE: DNA
<213> ORGANISM: Artificial Sequence
<220> FEATURE:
<223> OTHER INFORMATION: synthetic primer HER2_FAB_HC_STOP RP for PCR
      and RT-PCR

<400> SEQUENCE: 18
ttattaacaa caagatttcg gctccacct                                     29

<210> SEQ ID NO 19
<211> LENGTH: 24
<212> TYPE: DNA
<213> ORGANISM: Artificial Sequence
<220> FEATURE:
<223> OTHER INFORMATION: synthetic primer HER2_FAB_LC_STOP RP for PCR
      and RT-PCR

<400> SEQUENCE: 19
ttattagcac tcaccgcggt taaa                                          24
```

<210> SEQ ID NO 20
<211> LENGTH: 28
<212> TYPE: DNA
<213> ORGANISM: Artificial Sequence
<220> FEATURE:
<223> OTHER INFORMATION: synthetic primer FAB FP for PCR and RT-PCR

<400> SEQUENCE: 20
atggaagttc aattagtaga aagcggcg                                28

<210> SEQ ID NO 21
<211> LENGTH: 25
<212> TYPE: DNA
<213> ORGANISM: Artificial Sequence
<220> FEATURE:
<223> OTHER INFORMATION: synthetic primer FAB RP for PCR and RT-PCR

<400> SEQUENCE: 21
acaagatttc ggctccacct tcttg                                   25

<210> SEQ ID NO 22
<211> LENGTH: 25
<212> TYPE: DNA
<213> ORGANISM: Artificial Sequence
<220> FEATURE:
<223> OTHER INFORMATION: synthetic primer Fc FP for PCR and RT-PCR

<400> SEQUENCE: 22
caagaaggtg gagccgaaat cttgt                                   25

<210> SEQ ID NO 23
<211> LENGTH: 22
<212> TYPE: DNA
<213> ORGANISM: Artificial Sequence
<220> FEATURE:
<223> OTHER INFORMATION: synthetic primer Fc RP for PCR and RT-PCR

<400> SEQUENCE: 23
cttacccggg gacagggaca ag                                      22

<210> SEQ ID NO 24
<211> LENGTH: 35
<212> TYPE: DNA
<213> ORGANISM: Artificial Sequence
<220> FEATURE:
<223> OTHER INFORMATION: synthetic primer HC FP for PCR and RT-PCR

<400> SEQUENCE: 24
tatacatatg gaagttcaat tagtagaaag cggcg                        35

<210> SEQ ID NO 25
<211> LENGTH: 32
<212> TYPE: DNA
<213> ORGANISM: Artificial Sequence
<220> FEATURE:
<223> OTHER INFORMATION: synthetic primer HC RP for PCR and RT-PCR

<400> SEQUENCE: 25
ttttgtcgac cttacccggg gacagggaca ag                           32

<210> SEQ ID NO 26
<211> LENGTH: 20
<212> TYPE: DNA
<213> ORGANISM: Artificial Sequence
<220> FEATURE:

<223> OTHER INFORMATION: synthetic primer Univ TolA RP for PCR and RT-
          PCR

<400> SEQUENCE: 26
ttcagttgcc gctttctttc                                            20

<210> SEQ ID NO 27
<211> LENGTH: 35
<212> TYPE: DNA
<213> ORGANISM: Artificial Sequence
<220> FEATURE:
<223> OTHER INFORMATION: synthetic primer HER2 HCFAB Inner FP for PCR
      and RT-PCR

<400> SEQUENCE: 27
gagatatatc catggaagtt caattagtag aaagc                           35

<210> SEQ ID NO 28
<211> LENGTH: 29
<212> TYPE: DNA
<213> ORGANISM: Artificial Sequence
<220> FEATURE:
<223> OTHER INFORMATION: synthetic primer HER2 HCFAB Inner RP for PCR
      and RT-PCR

<400> SEQUENCE: 28
gaggcgatat aaagcttaca agatttcgg                                  29

<210> SEQ ID NO 29
<211> LENGTH: 18
<212> TYPE: DNA
<213> ORGANISM: Artificial Sequence
<220> FEATURE:
<223> OTHER INFORMATION: synthetic primer TolA Internal RP for PCR and
      RT-PCR

<400> SEQUENCE: 29
ctttggcggc ttctgctt                                              18

<210> SEQ ID NO 30
<211> LENGTH: 41
<212> TYPE: DNA
<213> ORGANISM: Artificial Sequence
<220> FEATURE:
<223> OTHER INFORMATION: synthetic primer T7F for scFv VH library
      construction

<400> SEQUENCE: 30
atacgaaatt aatacgactc actataggga gaccacaacg g                    41

<210> SEQ ID NO 31
<211> LENGTH: 20
<212> TYPE: DNA
<213> ORGANISM: Artificial Sequence
<220> FEATURE:
<223> OTHER INFORMATION: synthetic primer TolAR for scFv VH library
      construction

<400> SEQUENCE: 31
ttcagttgcc gctttctttc                                            20

<210> SEQ ID NO 32
<211> LENGTH: 45
<212> TYPE: DNA
<213> ORGANISM: Artificial Sequence
<220> FEATURE:
<223> OTHER INFORMATION: synthetic primer TolAkR for scFv VH library construction

<400> SEQUENCE: 32
ccgcacacca gtaaggtgtg cggtttcagt tgccgctttc tttct        45

<210> SEQ ID NO 33
<211> LENGTH: 54
<212> TYPE: DNA
<213> ORGANISM: Artificial Sequence
<220> FEATURE:
<223> OTHER INFORMATION: synthetic primer H1Fa for scFv VH library
      construction

<400> SEQUENCE: 33
cgcagcctct ggtttcaaca ttavtrrtwm ykmtatccac tgggtccgtc aggc        54

<210> SEQ ID NO 34
<211> LENGTH: 54
<212> TYPE: DNA
<213> ORGANISM: Artificial Sequence
<220> FEATURE:
<223> OTHER INFORMATION: synthetic primer H1Fb for scFv VH library
      construction

<400> SEQUENCE: 34
cgcagcctct ggtttcaaca ttavtrrtwm ykggatccac tgggtccgtc aggc        54

<210> SEQ ID NO 35
<211> LENGTH: 54
<212> TYPE: DNA
<213> ORGANISM: Artificial Sequence
<220> FEATURE:
<223> OTHER INFORMATION: synthetic primer H1Ra for scFv VH library
      construction

<400> SEQUENCE: 35
gcctgacgga cccagtggat akmrkwayya btaatgttga aaccagaggc tgcg        54

<210> SEQ ID NO 36
<211> LENGTH: 54
<212> TYPE: DNA
<213> ORGANISM: Artificial Sequence
<220> FEATURE:
<223> OTHER INFORMATION: synthetic primer H1Rb for scFv VH library
      construction

<400> SEQUENCE: 36
gcctgacgga cccagtggat ccmrkwayya btaatgttga aaccagaggc tgcg        54

<210> SEQ ID NO 37
<211> LENGTH: 76
<212> TYPE: DNA
<213> ORGANISM: Artificial Sequence
<220> FEATURE:
<223> OTHER INFORMATION: synthetic primer H2Fa for scFv VH library
      construction

<400> SEQUENCE: 37
gggtaaaggc ctggaatggg ttgstdggat tdmtccgdmt rrcggtdmta cgdactacgc        60
cgatagcgtg aaaggc        76

<210> SEQ ID NO 38
<211> LENGTH: 76
<212> TYPE: DNA
<213> ORGANISM: Artificial Sequence
<220> FEATURE:

<223> OTHER INFORMATION: synthetic primer H2Fb for scFv VH library
      construction

<400> SEQUENCE: 38
gggtaaaggc ctggaatggg ttgstdhtat tdmtccgdmt rrcggtdmta cgdactacgc    60
cgatagcgtg aaaggc                                                   76

<210> SEQ ID NO 39
<211> LENGTH: 76
<212> TYPE: DNA
<213> ORGANISM: Artificial Sequence
<220> FEATURE:
<223> OTHER INFORMATION: synthetic primer H2Fc for scFv VH library
      construction

<400> SEQUENCE: 39
gggtaaaggc ctggaatggg ttgstgaaat tdmtccgdmt rrcggtdmta cgdactacgc    60
cgatagcgtg aaaggc                                                   76

<210> SEQ ID NO 40
<211> LENGTH: 76
<212> TYPE: DNA
<213> ORGANISM: Artificial Sequence
<220> FEATURE:
<223> OTHER INFORMATION: synthetic primer H2Ra for scFv VH library
      construction

<400> SEQUENCE: 40
gcctttcacg ctatcggcgt agthcgtakh accgyyakhc ggakhaatcc hascaaccca    60
ttccaggcct ttaccc                                                   76

<210> SEQ ID NO 41
<211> LENGTH: 76
<212> TYPE: DNA
<213> ORGANISM: Artificial Sequence
<220> FEATURE:
<223> OTHER INFORMATION: synthetic primer H2Rb for scFv VH library
      construction

<400> SEQUENCE: 41
gcctttcacg ctatcggcgt agthcgtakh accgyyakhc ggakhaatad hascaaccca    60
ttccaggcct ttaccc                                                   76

<210> SEQ ID NO 42
<211> LENGTH: 76
<212> TYPE: DNA
<213> ORGANISM: Artificial Sequence
<220> FEATURE:
<223> OTHER INFORMATION: synthetic primer H2Rc for scFv VH library
      construction

<400> SEQUENCE: 42
gcctttcacg ctatcggcgt agthcgtakh accgyyakhc ggakhaattt cascaaccca    60
ttccaggcct ttaccc                                                   76

<210> SEQ ID NO 43
<211> LENGTH: 79
<212> TYPE: DNA
<213> ORGANISM: Artificial Sequence
<220> FEATURE:
<223> OTHER INFORMATION: synthetic primer H3Fa for scFv VH library
      construction
<220> FEATURE:
<221> NAME/KEY: modified_base
<222> LOCATION: (1)...(79)
<223> OTHER INFORMATION: n = g, a, c or t

<400> SEQUENCE: 43
cggaagatac cgccgtttat tactgtgcgc gcnnknnknn knnknnknnk nnknnkatgg      60
actactgggg tcagggcac                                                  79

<210> SEQ ID NO 44
<211> LENGTH: 81
<212> TYPE: DNA
<213> ORGANISM: Artificial Sequence
<220> FEATURE:
<223> OTHER INFORMATION: synthetic primer H3Fb for scFv VH library
      construction
<220> FEATURE:
<221> NAME/KEY: modified_base
<222> LOCATION: (1)...(81)
<223> OTHER INFORMATION: n = g, a, c or t

<400> SEQUENCE: 44
cggaagatac cgccgtttat tactgtgcgc gcnnknnknn knnknnknnk nnknnktttg      60
actactgggg tcagggcacc c                                               81

<210> SEQ ID NO 45
<211> LENGTH: 79
<212> TYPE: DNA
<213> ORGANISM: Artificial Sequence
<220> FEATURE:
<223> OTHER INFORMATION: synthetic primer H3Ra for scFv VH library
      construction
<220> FEATURE:
<221> NAME/KEY: modified_base
<222> LOCATION: (1)...(79)
<223> OTHER INFORMATION: n = g, a, c or t

<400> SEQUENCE: 45
gtgccctgac cccagtagtc catmnnmnnm nmnnmnnmn nmnnmnngcg cgcacagtaa       60
taaacggcgg tatcttccg                                                  79

<210> SEQ ID NO 46
<211> LENGTH: 81
<212> TYPE: DNA
<213> ORGANISM: Artificial Sequence
<220> FEATURE:
<223> OTHER INFORMATION: synthetic primer H3Rb for scFv VH library
      construction
<220> FEATURE:
<221> NAME/KEY: modified_base
<222> LOCATION: (1)...(81)
<223> OTHER INFORMATION: n = g, a, c or t

<400> SEQUENCE: 46
gggtgccctg accccagtag tcaaamnnmn nmnnmnnmnn mnnmnnmnng cgcgcacagt      60
aataaacggc ggtatcttcc g                                               81

<210> SEQ ID NO 47
<211> LENGTH: 34
<212> TYPE: DNA
<213> ORGANISM: Artificial Sequence
<220> FEATURE:
<223> OTHER INFORMATION: synthetic primer VLF for scFv VH library
      construction

<400> SEQUENCE: 47
gatatatcca tggatattca aatgacccaa tctc                                 34

```
<210> SEQ ID NO 48
<211> LENGTH: 29
<212> TYPE: DNA
<213> ORGANISM: Artificial Sequence
<220> FEATURE:
<223> OTHER INFORMATION: synthetic primer VHR for scFv VH library
      construction

<400> SEQUENCE: 48
cgatataaag cttggaactg acggtaacc                                             29

<210> SEQ ID NO 49
<211> LENGTH: 34
<212> TYPE: DNA
<213> ORGANISM: Artificial Sequence
<220> FEATURE:
<223> OTHER INFORMATION: synthetic primer VLR for scFv VH library
      construction

<400> SEQUENCE: 49
gagattgggt catttgaata tccatggata tatc                                       34

<210> SEQ ID NO 50
<211> LENGTH: 29
<212> TYPE: DNA
<213> ORGANISM: Artificial Sequence
<220> FEATURE:
<223> OTHER INFORMATION: synthetic primer VHF for scFv VH library
      construction

<400> SEQUENCE: 50
ggttaccgtc agttccaagc tttatatcg                                             29

<210> SEQ ID NO 51
<211> LENGTH: 45
<212> TYPE: DNA
<213> ORGANISM: Artificial Sequence
<220> FEATURE:
<223> OTHER INFORMATION: synthetic primer BsaI-VLF for scFv VH library
      construction

<400> SEQUENCE: 51
aaaaaggtct cctatggata ttcaaatgac ccaatctccg tcttc                           45

<210> SEQ ID NO 52
<211> LENGTH: 41
<212> TYPE: DNA
<213> ORGANISM: Artificial Sequence
<220> FEATURE:
<223> OTHER INFORMATION: synthetic primer BsaI-VHR for scFv VH library
      construction

<400> SEQUENCE: 52
aaaaaaggtc tccccgcgga actgacggta accagggtgc c                               41
```

USE OF LAMBDA-GAM PROTEIN IN RIBOSOMAL DISPLAY TECHNOLOGY

CROSS-REFERENCES TO RELATED APPLICATIONS

This application is a Divisional of application Ser. No. 14/786,147, filed Oct. 21, 2015, which is a National Stage of International Application No. PCT/US2014/035325, filed Apr. 24, 2014, which claims the benefit of priority to U.S. Provisional Application No. 61/815,951, filed Apr. 25, 2013, the disclosures of each of which are incorporated by reference herein in their entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 091200-1067915-006020US-SEQLIST.TXT-, created on Jan. 8, 2018, 15,635 bytes, machine format IBM-PC, MS-Windows operating system, is hereby incorporated by reference in its entirety for all purposes.

BACKGROUND OF THE INVENTION

Ribosomal display is a cell-free system using the principle of coupling phenotype (protein) to genotype (gene) for the in vitro selection of proteins from large libraries (Mattheakis et al., *Proc. Natl. Acad. Sci. USA*, 91:9022-9026 (1994); Hanes et al., *Proc. Natl. Acad. Sci. USA*, 94:4937-4942 (1997); He et al., Nucleic Acids Res. 25(24):5132-4 (1997)). Prokaryotic and eukaryotic ribosomal display systems have been used for the selection of peptides, single-chain antibodies (e.g., scFvs), enzymes, stable protein scaffolds and other ligand-binding domains (He et al., *Brief Funct. Genomic Proteomic*, 1(2):204-12 (2002)). The methods described herein increase the efficiency of ribosomal display methods for producing and selecting proteins of interest from very large libraries (e.g., between about $10^3$ to $10^5$ members, or about $10^5$ to $10^{16}$ members).

BRIEF SUMMARY OF THE INVENTION

The present disclosure is directed to methods and systems for increasing the stability of a nucleic acid template that encodes a protein of interest in a cell free translation system or a ribosomal display reaction system. In some embodiments, the nucleic acid template is an RNA or mRNA. The stability of the RNA template is increased by adding the bacteriophage lambda protein Gam to the cell free extract used in the translation system. The addition of Gam protein increases the efficiency of the ribosomal display reaction system. Thus, is one aspect, a method of stabilizing a protein encoding RNA in a ribosomal display reaction system is described, the method comprising the step of: combining a nucleic acid template encoding a protein of interest and lacking a operable stop codon with a cell free translation system to yield a ribosomal display reaction system containing a complex of the mRNA encoding the protein of interest, a ribosome and the protein of interest, wherein the system has a concentration of Gam protein sufficient to stabilize the mRNA encoding the protein of interest.

In another aspect, a ribosomal display reaction system is provided, the ribosomal display reaction system comprising a mRNA encoding a protein of interest without an operable stop codon, a cell free translation system, and a concentration of Gam protein sufficient to stabilize the mRNA encoding the protein of interest.

In a third aspect, a method of selecting for a protein of interest using a ribosomal display reaction system is described, the method comprising:
  i) combining a library of nucleic acid members, each member encoding a prospective protein of interest having a primary amino acid different from the other proteins encoded by the other nucleic acid members, and where the members lack an operable stop codon, with a cell free translation system to yield a ribosomal display reaction system containing a mixture of different complexes, each complex comprising a different mRNA encoding the prospective protein of interest, a ribosome, and a prospective protein of interest, wherein the system has a concentration of Gam protein sufficient to stabilize the mRNA encoding the protein of interest; and,
  ii) selecting proteins of interest from the ribosomal display reaction system by binding the complexes to an immobilized binding pair ligand that binds to proteins of interest.

DEFINITIONS

Figure 1:
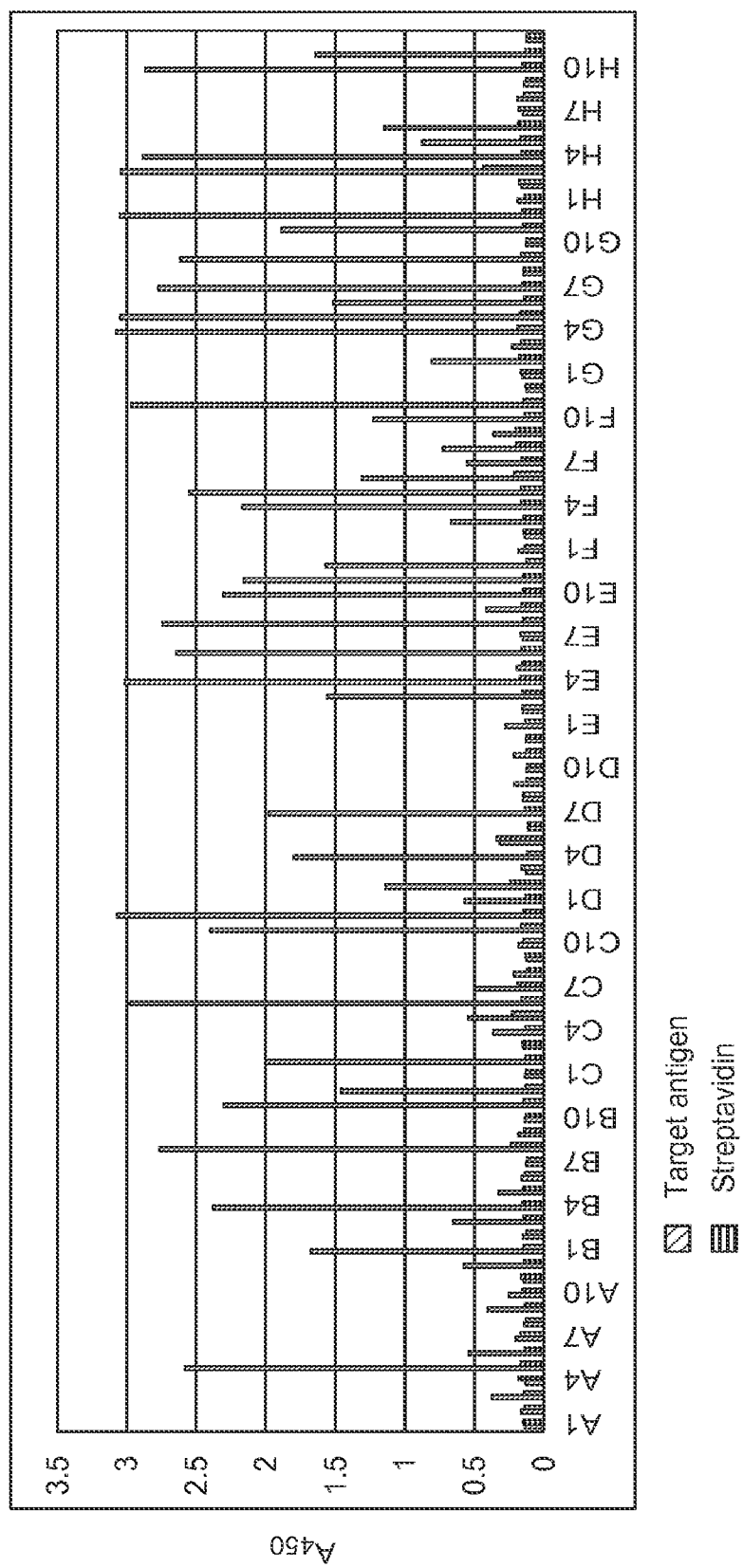
FIG. 1 shows ELISA data of selected scFvs in extract reformatted to scFvFcs showing specific binding to the target antigen with respect to streptavidin.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier ($4^{th}$ ed. 2007); Sambrook et al., MOLECULAR CLONING, A LABORATORY MANUAL, Cold Springs Harbor Press (Cold Springs Harbor, N.Y. 1989); Ausubel et al., CURRENT PROTOCOLS IN MOLECULAR BIOLOGY, John Wiley and Sons (Hoboken, N.Y. 1995). The term "a" or "an" is intended to mean "one or more." The term "comprise" and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

The term "λGam" refers to a Gam protein of the enterobacteria phage lambda that inhibits the RecBCD nuclease of host bacteria. A λGam protein generally includes proteins having an amino acid sequence with greater than about 50% identity, greater than about 60% identity, greater than about 70% identity, or greater than about 80%, 85%, 90%, 92%, 93%, 94%, 95%, 96%, 97%, 98%, or 99% amino acid sequence identity with a λGam protein, with the amino acid identity determined using a sequence alignment program such as BLASTP, CLUSTALW and EMBOSS Needle, as described herein. Such proteins can be prepared, for example, by purification of host bacteria such as *E. coli*, by recombinant expression of a nucleic acid encoding a λGam protein, and by synthetic means such as solution or solid phase peptide synthesis.

The term "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), and single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. See, Huston, et al. (1988) Proc. Nat. Acad. Sci. USA, 85: 5879-5883. While the VH and VL are connected to each as a single polypeptide chain, the VH and VL domains associate non-covalently. The first functional antibody molecules to be expressed on the surface of filamentous phage were single-chain Fv's (scFv); however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies include all those that have been displayed on phage (e.g., scFv, Fv, Fab and disulfide linked Fv (Reiter et al. (1995) Protein Eng. 8: 1323-1331). Antibodies can also include diantibodies, miniantibodies and scFv-Fc fusions.

The term "bacterial derived cell free extract" refers to preparation of in vitro reaction mixtures able to translate mRNA into polypeptides. The mixtures include ribosomes, ATP, amino acids, and tRNAs. The extract may be derived directly from lysed bacteria, from purified components or combinations of both.

The term "cell free protein synthesis system" or "cell free translation system" refers to a system for the in vitro synthesis of polypeptides in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc.; and co-factors, enzymes and other reagents that are necessary for the synthesis, e.g. ribosomes, uncharged tRNAs, tRNAs charged with natural and/or unnatural amino acids, polymerases, transcriptional factors, tRNA synthetases, etc. In some embodiments, the cell free protein synthesis system comprises a bacterial cell free extract.

The term "library of nucleic acid members" refers to a collection of different nucleic acid species or members where each member has a nucleic acid sequence that differs from the sequence of the other members of the library. Each member of the library can encode a different protein of interest, such that each protein of interest has a different primary amino acid sequence than other proteins encoded by other members of the library. The library members can differ randomly, stochastically, or with directed mutations of particular nucleic acids. In some embodiments, the library members encode an antibody or fragment thereof, for example a $V_H$ or $V_L$ chain peptide domain. In some embodiments, the library members encode an scFv. Thus, the library can be an antibody library, which refers to a plurality of nucleic acid molecules (e.g., DNA or RNA) containing an open reading frame (ORF) that encodes an antibody or fragment thereof or a plurality of peptides comprising antibodies or fragments thereof. It also includes a plurality of antibody peptides and nucleic acid/antibody fusion molecules expressed from said DNA or RNA molecules.

The term "complex of nucleic acid encoding the protein of interest, a ribosome, and a protein of interest" refers to the ternary complexes formed during the ribosomal display process. The complexes include the nucleic acid (e.g., mRNA) encoding the protein of interest that is attached or tethered to the ribosome, the ribosome (including the various ribosomal protein and RNA subunits), and the translated polypeptide representing the protein of interest. The nucleic acid sequence can include a "ribosome trapping sequence" that functions to tether the nucleic acid template to the ribosome. The ribosome trapping sequence can be from about 30-100 codons in length, does not include a stop codon, and is expressed "in frame" with the coding region of the protein of interest. By tethering the RNA template to the ribosome, the polypeptide that is translated from the RNA template can emerge from the ribosome tunnel and fold into a tertiary structure outside the ribosome while still tethered to the RNA template. A ribosome trapping sequence may also be constructed using the methods of mRNA display (Takahashi et al., *Trends Biochem. Sci.* 28:159-165, 2003). In mRNA display the encoded protein is covalently attached to the RNA using a 3' puromycin tagged RNA. Puromycin is a translation inhibitor that is able to enter the ribosome during translation and form a stable covalent bond with the nascent protein. This allows a stable covalent linkage to be formed between the mRNA display template and the protein it encodes, resulting in an mRNA-displayed protein. In some embodiments, the complex further includes a polypeptide that specifically binds to the protein of interest (e.g., a $V_H$ chain that binds to a $V_L$ chain), in which case the complex is referred to as a quaternary complex.

As used herein, the term "functional stop codon" or "operable stop codon" refers to a nucleotide triplet within messenger RNA that signals a termination of translation. Stop codons signal the termination of this process by binding release factors, which cause the ribosomal subunits to disassociate, releasing the amino acid chain. In RNA the stop codons are UAG ("amber"); UAA ("ochre") and UGA ("opal"). The corresponding codons in DNA are TAG ("amber") TAA ("ochre") and TGA ("opal" or "umber"). When a template lacks a functional or operable stop codon, one of these codons is not present.

The term "ribosomal display reaction system" refers to a reaction system able to yield a ternary complex of an mRNA, ribosome and corresponding protein of interest. Ribosomal display can be used for screening antibodies and fragments thereof for target antigen binding. The steps of producing the reaction system can include: 1) generating a DNA library and transcribing the library into an RNA library, 2) purifying the RNA and in vitro translation in a cell-free protein synthesis system, 3) allowing the ribosome complexes of the translation reaction to bind to a target antigen, 4) selecting bound ribosome complexes; and 5) isolating RNA from the complexes and reverse transcribing the transcripts to cDNA, wherein the cDNA can be amplified, sequenced and/or further modified.

The terms "specific for," "specifically binds," and the like refer to the binding of a molecule (e.g., antibody or antibody fragment) to a target (antigen, epitope, antibody target, etc.) with at least 2-fold greater affinity than non-target compounds, e.g., at least 4-fold, 5-fold, 6-fold, 7-fold, 8-fold, 9-fold, 10-fold, 20-fold, 25-fold, 50-fold, or 100-fold greater affinity. For example, a Fab fragment that specifically binds, or is specific for, a target is a Fab fragment that will typically bind its target antigen with at least a 2-fold greater affinity than a non-target antigen.

The term "nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA.

The term "nucleic acid template" includes a DNA or RNA polynucleotide from which a polypeptide will be translated. It will be understood by those of skill in the art that a DNA nucleic acid template must first be transcribed into RNA, and that the RNA is translated into a polypeptide. DNA can be transcribed into RNA either in vivo or in vitro. The methods of in vitro transcription of a DNA template are well known in the art. In some embodiments, the DNA template is subject to simultaneous in vitro transcription and translation.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

The term "peptide," "protein," and "polypeptide" are used herein interchangeably and refer to a to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins and truncated proteins, wherein the amino acid residues are linked by covalent peptide bonds.

The terms "identical" or percent "identity," in the context of two or more nucleic acids or polypeptide sequences, refer to two or more sequences or subsequences that are the same or have a specified percentage of nucleotides or amino acid residues that are the same (e.g., 60% identity, optionally 65%, 70%, 75%, 80%, 85%, 90%, 95%, 97% or 99% identity over a specified region), when compared and aligned for maximum correspondence over a comparison window, or designated region, as measured using the BLAST and PSI-BLAST algorithms, which are described in Altschul et al. (J. Mol. Biol. 215:403-10, 1990), and Altschul, et al. (Nucleic Acids Res., 25:3389-3402, 1997), respectively. Software for performing BLAST analyses is publicly available through the National Center for Biotechnology Information (see the internet at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915, 1989) alignments (B) of 50, expectation (E) of 10, M=5, N=−4, and a comparison of both strands. Pairwise sequence alignment of nucleotide and protein sequences can also be performed using EMBOSS Needle and the following default settings: Matrix: BLOSUM62; Gap open: 10; Gap extend 0.5; output format: pair; end gap penalty: false; end gap open: 10; end gap extend: 0.5 (see the internet at ebi.ac.uk/Tools/psa/emboss needle/). Multiple sequence alignments of nucleotide and amino acid sequences can be performed using the Clustal Omega tool and the following default settings: Dealign input sequences: No (false); Output alignment format: Clustal; MBED-like clustering guide tree: yes (true); MBED-like clustering interation: yes (true); Number of combined iterations: default(0) [0]; Max guide tree interation: default [−1]; Max HMM iterations: default [−1] (see the internet at ebi.ac.uk/Tools/msa/clustalo/).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art.

The BLAST algorithm also performs a statistical analysis of the similarity between two sequences (see, e.g., Karlin and Altschul, *Proc. Natl. Acad. Sci. USA* 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

When percentage of sequence identity is used in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made using well-known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using the algorithm described in Pearson et al. (*Meth. Mol. Biol.* 24:307-331, 1994). Alignment also can be performed by simple visual inspection and manual alignment of sequences.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a protein variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein.

Furthermore, it will be recognized that individual substitutions, deletions or additions that alter, add or delete a single amino acid or a small percentage of amino acids (typically less than 10%, and generally less than 1%) in an encoded sequence can be considered conservatively modified variations, provided alteration results in the substitution of an amino acid with a chemically similar amino acid. Conservative amino acid substitutions providing functionally similar amino acids are well known in the art, including the following six groups, each of which contains amino acids that are considered conservative substitutes for each another:

1) Alanine (Ala, A), Serine (Ser, S), Threonine (Thr, T);
2) Aspartic acid (Asp, D), Glutamic acid (Glu, E);
3) Asparagine (Asn, N), Glutamine (Gln, Q);
4) Arginine (Arg, R), Lysine (Lys, K)
5) Isoleucine (Ile, I), Leucine (Leu, L), Methionine (Met, M), Valine (Val, V); and
6) Phenylalanine (Phe, F), Tyrosine (Tyr, Y), Tryptophan (Trp, W).

Two or more amino acid sequences or two or more nucleotide sequences are considered to be "substantially similar" if the amino acid sequences or the nucleotide sequences share at least 50%, 60%, 65%, 70%, 75%, 80%, 85%, 90%, 95% or 99% sequence identity with each other, or with a reference sequence over a given comparison window.

DETAILED DESCRIPTION OF THE INVENTION

Introduction

The methods and systems described herein are useful for stabilizing an mRNA encoding a protein of interest and for selecting a protein of interest in a ribosomal display reaction system. The inventors have surprisingly discovered that adding the bacteriophage lambda Gam protein to the ribosomal display reaction system increases the stability of the mRNA template encoding the protein of interest. While it is well known that Gam can inhibit the degradation of double-stranded linear DNA by bacterial nucleases, the methods described herein are useful for increasing the stability of an RNA template in a ribosome display complex. Thus, adding λGam increased the longevity of the reaction systems, allowing for more efficient production and selection of the protein of interest. The methods and systems will now be described.

In one aspect, the methods described herein use a ribosomal display reaction system (RDRS). The RDRS comprises a nucleic acid template encoding the protein of interest, wherein the nucleic acid template lacks an operable stop codon. The absence of a stop codon prevents the nascent polypeptide from being released from the ribosomal complex comprising the RNA template, a ribosome, and the protein of interest. Thus, the protein of interest can be subjected to functional studies and/or selection for improved activity (e.g., binding to a target molecule), while still tethered to the RNA encoding the protein of interest. This allows the sequence of the RNA encoding the improved protein of interest to be determined, for example, by reverse transcription, amplification, and sequencing of the amplified nucleic acid, which thereby allows the amino acid sequence of the protein of interest to be determined. In some embodiments, the nucleic acid template is RNA that is transcribed from a DNA construct.

The nucleic acid template encoding the protein of interest and lacking an operable stop codon is combined with a cell free translation system to produce the RDRS, wherein the RDRS comprises a complex of the nucleic acid template encoding the protein of interest, a ribosome, and the protein of interest. In some embodiments, the RDRS comprises a Gam protein in a concentration sufficient to stabilize the nucleic acid template (e.g., mRNA) encoding the protein of interest. For example, in some embodiments, the concentration of Gam in the extract used for the cell free translation system can be about 25-60 ug/ml of extract. In some embodiments, the Gam protein is from bacteriophage lambda (λGam). In some embodiments, the Gam protein is the S form of the protein.

In another aspect, a ribosomal display reaction system is provided, the RDRS comprising an mRNA encoding a protein of interest (POI), wherein the mRNA lacks an operable stop codon. The RDRS further comprises a cell free translation system and has a concentration of λGam protein sufficient to stabilize the mRNA encoding the protein of interest.

In another aspect, a method of selecting a protein of interest using a ribosomal display reaction system is described. The method comprises the step of combining a library of nucleic acid members with a cell free translation system to yield a ribosomal display reaction system. Each member of the library encodes a prospective protein of interest having a primary amino acid sequence different from the other proteins encoded by the other nucleic acid members. As above, the members of the nucleic acid library lack an operable stop codon. The RDRS contains a mixture of different complexes, where each complex comprises a different mRNA encoding a prospective POI, a ribosome and a prospective protein of interest. The system has a concentration of λGam protein sufficient to stabilize the POI encoding mRNA. The method further comprises a second step of selecting proteins of interest from the RDRS by binding the complexes to an immobilized binding pair ligand that binds to the proteins of interest. In some embodiments, the RNA of the complexes of step two are amplified and reintroduced into a second cell free translation system to yield a second RDRS enriched for proteins of interest that are able to bind to the immobilized binding pair ligand.

In the above aspects and embodiments, the protein of interest can be an antibody. In some embodiments, the protein of interest is a single chain antibody. In some embodiments, the RDRS comprises two or more nucleic acid templates wherein each template encodes a protein of interest having a different primary amino acid sequence from the other templates. In one embodiment, the method further comprises the step of capturing the protein of interest to a binding pair member that is immobilized to a support substrate. The term "binding pair member" refers to one member of a pair of molecules, where one member of the pair specifically binds to the other member of the binding pair. Non-limiting examples of binding pair members include antibody-antigen, ligand-receptor, nucleic acid binding proteins-target nucleic acids, etc. In some embodiments, the capturing step is repeated to enrich for optimal binding of the protein of interest.

General Methods

Unless defined otherwise, all technical and scientific terms used herein have the meaning commonly understood by one of ordinary skill in the art to which this invention belongs. Practitioners are particularly directed to Green, M. R., and Sambrook, J., eds., Molecular Cloning: A Laboratory Manual, 4th ed., Cold Spring Harbor Laboratory Press, Cold Spring Harbor, N.Y. (2012), and Ausubel, F. M., et al., Current Protocols in Molecular Biology (Supplement 99), John Wiley & Sons, New York (2012), which are incorporated herein by reference, for definitions and terms of the art. Standard methods also appear in Bindereif, Schon, & Westhof (2005) Handbook of RNA Biochemistry, Wiley-VCH, Weinheim, Germany which describes detailed methods for RNA manipulation and analysis, and is incorporated herein by reference. Examples of appropriate molecular techniques for generating recombinant nucleic acids, and instructions sufficient to direct persons of skill through many cloning exercises are found in Green, M. R., and Sambrook, J (Id.); Ausubel, F. M., et al., (Id.); Berger and Kimmel, Guide to Molecular Cloning Techniques, Methods in Enzymology (Volume 152 Academic Press, Inc., San Diego, Calif. 1987); and PCR Protocols: A Guide to Methods and Applications (Academic Press, San Diego, Calif. 1990), which are incorporated by reference herein.

Methods for protein purification, chromatography, electrophoresis, centrifugation, and crystallization are described in Coligan et al. (2000) Current Protocols in Protein Science, Vol. 1, John Wiley and Sons, Inc., New York. Methods for cell-free synthesis are described in Spirin & Swartz (2008) Cell-free Protein Synthesis, Wiley-VCH, Weinheim, Germany. Methods for incorporation of non-native amino acids into proteins using cell-free synthesis are described in Shimizu et al (2006) FEBS Journal, 273, 4133-4140.

PCR amplification methods are well known in the art and are described, for example, in Innis et al., PCR Protocols: A Guide to Methods and Applications, Academic Press Inc. San Diego, Calif., 1990. An amplification reaction typically includes the DNA that is to be amplified, a thermostable DNA polymerase, two oligonucleotide primers, deoxynucleotide triphosphates (dNTPs), reaction buffer and magnesium. Typically a desirable number of thermal cycles is between 1 and 25. Methods for primer design and optimization of PCR conditions are well known in the art and can be found in standard molecular biology texts such as Ausubel et al., Short Protocols in Molecular Biology, 5$^{th}$ Edition, Wiley, 2002, and Innis et al., PCR Protocols, Academic Press, 1990. Computer programs are useful in the design of primers with the required specificity and optimal amplification properties (e.g., Oligo Version 5.0 (National Biosciences)). In some embodiments, the PCR primers may additionally contain recognition sites for restriction endonucleases, to facilitate insertion of the amplified DNA fragment into specific restriction enzyme sites in a vector. If restriction sites are to be added to the 5' end of the PCR primers, it is preferable to include a few (e.g., two or three) extra 5' bases to allow more efficient cleavage by the enzyme. In some embodiments, the PCR primers may also contain an RNA polymerase promoter site, such as T7 or SP6, to allow for subsequent in vitro transcription. Methods for in vitro transcription are well known to those of skill in the art (see, e.g., Van Gelder et al., Proc. Natl. Acad. Sci. U.S.A. 87:1663-1667, 1990; Eberwine et al., Proc. Natl. Acad. Sci. U.S.A. 89:3010-3014, 1992).

I. Ribosomal Display Systems

In order to perform the methods described herein, one needs a ribosomal display reaction system. Ribosomal display can be used to perform in vitro protein synthesis of a protein of interest. Ribosomal display can also be used to perform in vitro protein evolution to create proteins with desired properties, for example, Fab fragments that bind to a specific target molecule. Ribosomal display is a well-known technology useful for generating libraries. This entirely in vitro method allows for libraries with a diversity of $10^{16}$ members. The process results in translated proteins that are associated with their RNA progenitor which can be used, as a complex, to select for proteins with desired properties (e.g., bind to an immobilized target molecule). The RNA-protein complex that shows the desired property, e.g., high binding affinity, can then be reverse transcribed to cDNA and the sequence amplified via PCR. The process also provides for repeated cycles of iteration or protein expression. In addition, nucleic acid mutations can be introduced efficiently into the selected nucleic acid library in subsequent cycles, leading to continuous DNA diversification and thus, protein evolution. The end result is a nucleic acid sequence that can be used to produce a protein of interest (e.g., Fab fragments that specifically bind to the target antigen).

In the method provided herein, a protein of interest is displayed on the surface of a ribosome from which the protein of interest is being translated. Briefly, a library of RNA molecules is translated in an in vitro translation system to the 3' end of the RNA molecule, such that the ribosome does not fall off. This is accomplished by not incorporating a functional stop codon in the RNA template. Normally, the stop codon is recognized by release factors that trigger detachment of the nascent polypeptide from the ribosome. In ribosomal display, the peptide emerges from the ribosome, but does not fall free of the complex. This allows, for example, the nascent polypeptide to associate with another polypeptide to form a functional dimer. In some instances, there is an additional folding step in an oxiding environment (important for forming disulfide bonds).

The whole complex of folded protein of interest, ribosome and RNA, which is stable for several days, can then be screened for desired properties, such as specific binding to a binding pair ligand by the translated protein of interest. The RNA encoding the selected protein of interest can be reverse transcribed into single stranded cDNA which can be converted to double-stranded DNA and amplified by PCR, providing the coding sequence of the selected protein (e.g., an antibody or single chain antibody). The reverse transcription reaction can be performed on mRNA associated in the ribosomal display complex, or the mRNA can be isolated from the ribosomal display complex then used in the reverse transcription step. Suitable methods for disruption/dissociation of ribosome complexes are known in the art and include EDTA treatment and/or phenol extraction.

In general, nucleic acid (DNA) constructs for ribosomal display contain a promoter (T7, SP6 or T3), a translation initiation signal such as a Shine-Dalgarno (prokaryotic) or Kozak (eukaryotic) sequence, initiation codon, and coding sequence of the protein of interest (e.g., $V_H$ or $V_L$ chain domain). One or more nucleic acid sequences encoding one or more detection tags may be included to provide for production of a protein further comprising one or more detection tags (e.g., histidine tag). To enable the complete nascent protein to be displayed and fold into its active conformation, a spacer domain of at least 23-30 amino acids length can be added at the C terminus, to allow the protein to exit completely from the ribosome. The spacer can provide a known sequence for the design of primers for RT-PCR recovery of the DNA sequences.

To remove the stop codon from DNA, a 3' primer lacking the stop codon can be used during PCR construction. Constructs designed for bacterial-based display systems can incorporate sequences containing stem-loop structures at the 5' and 3' ends of the DNA to stabilize mRNA against degradation by RNase activities in bacterial cell-free systems.

The mRNA translation system used in the methods described herein may be any suitable available system. A prokaryotic or eukaryotic translation system may be used, for example crude E. coli lysate (commercially available from e.g. Promega Corp., Madison, Wis.; Agilent Technologies, Santa Clara, Calif.; GE Healthcare Biosciences, Pittsburgh, Pa.; Life Technologies, Carlsbad, Calif.), a reconstituted ribosome system such as PURE (see, e.g., Shimizu et al., *Nat. Biotechnol.*, 19:751-755 (2001)), or a cell free protein synthesis system as described below.

The PURE system can include about 32 individually purified components used for in vitro protein biosynthesis (e.g., initiation, elongation and termination). In some embodiments, the components include initiation factors (e.g., IF1, IF2, IF3), elongation factors (e.g., EF-G, EF-Tu, EF-Ts), release factors (e.g., RF1, RF3), a termination factor (e.g., RRF), 20 aminoacyl-tRNA synthetases, methionyl-tRNA transformylase, T7 RNA polymerase, ribosomes, 46 tRNAs, NTPs, creatine phosphate, 10-formyl-5,6,7,8-tetra-hydrofolic acid, 20 amino acids, creatine kinase, myokinase, nucleoside-diphophate kinase and pryophosphatase.

Ribosomal display has been used to successfully generate antibody fragments with high affinity for their target. Detailed description of ribosomal display is found in, e.g., Hanes, *J. Proc. Natl. Acad. Sci. USA*, 95: 14130-14135 (1998); Schaffitzel et al., *J. Immunological Methods*, 231: 119-135 (1999); He et al., *J. Immunological Methods*, 231, 105-117 (1999); Roberts R W, *Current Opinion in Chemical Biology*, 3: 268-273 (1999).

II. Other Display Methods for In Vitro Selection

Other in vitro library display methods can be used in the methods described herein, such as, but not limited to, mRNA display, bicistronic display, P2A display, and CIS display (cis-activity display).

A. mRNA Display

In mRNA display, each member of the RNA library is directly attached to the protein of interest it encodes by a stable covalent linkage to puromycin, an antibiotic that can mimic the aminoacyl end of tRNA (see, e.g., Robert R W and Szostak J W, *Proc. Natl. Acad. Sci. USA*, 94:12297-12302 (1997)). Puromycin is an aminonucleoside antibiotic, active in either prokaryotes or eukaryotes, derived from *Streptomyces alboniger*. Protein synthesis is inhibited by premature chain termination during translation taking place in the ribosome. Part of the molecule acts as an analog of the 3' end of a tyrosyl-tRNA, where a part of its structure mimics a molecule of adenosine and another part mimics a molecule of tyrosine. It enters the A site and transfers to the growing chain, causing the formation of a puromycylated nascent chain and premature chain release. The 3' position contains an amide linkage instead of the normal ester linkage of tRNA, making the molecule much more resistant to hydrolysis and stopping procession along the ribosome.

Other puromycin analog inhibitors of protein synthesis include O-demethylpuromycin, O-propargyl-puromycin, 9-{3'-deoxy-3'-[(4-methyl-L-phenylalanyl)amino]-β-D-ri-bofuranosyl}-6-(N,N'-dimethylamino)purine [L-(4-Me)-Phe-PANS] and 6-dimethylamino-9-[3-(p-azido-L-beta-phenylalanylamino)-3-deoxy-beta-ribofuranosyl] purine.

Members of the RNA library can be ligated to puromycin via a linker such as, but not limited to, a polynucleotide or a chemical linker, e.g., polyethylene glycol (Fukuda et al., *Nucleic Acid Research*, 34(19):e127 (2006)). In some embodiments, the polynucleotide linker comprising RNA is linked at the 3' terminal end to puromycin. In other embodiments, the PEG liker is linked to puromycin.

As puromycin that is linked to the 3' terminal end of a RNA molecule enters a ribosome, it establishes a covalent bond to the nascent protein (encoded by the RNA molecule) as a result of peptidyl transferase activity in the ribosome. In turn, a stable amide linkage forms between the protein and the O-methyl tyrosine portion of puromycin.

The RNA library of RNA-puromycin fusions can undergo in vitro translation, as described herein, to generate RNA-puromycin-protein complexes (e.g., RNA-puromycin-Fab fragment complexes). In some embodiments, the RNA-puromycin fusions comprise RNA molecules encoding $V_H$ chains. In some embodiments, the RNA-puromycin fusions comprise RNA molecules encoding $V_L$ chains.

Affinity selection can be performed on the mRNA-displayed protein library to screen for proteins having desired properties, such a specific binding to a binding pair ligand. The mRNA display can be performed in solution or on a solid support. The selected mRNA-displayed protein of interest can be purified by standard methods known in the art such as affinity chromatography. The mRNA can be cloned, PCR amplified, and/or sequenced to determine the coding sequence of the selected protein of interest. In one embodiment, the selected mRNA-displayed library contains a population of $V_H$ chains. In one embodiment, the selected mRNA-displayed library contains a population of $V_H$ chains.

In some aspects, members of a library of nucleic acid members are linked to puromycin, where each member encodes a prospective protein of interest having a primary amino acid sequence different from the other proteins encoded by the other nucleic acid members. The mRNA display system can contain a population or mixture of different complexes such that each complex has a different mRNA linked to puromycin, the ribosome, and a prospective protein of interest.

B. Biscistronic DNA Display

Bicistronic DNA display can be employed for in vitro selection of proteins of interest (see, e.g., Sumida et al., *Nucleic Acid Research*, 37(22):e147 (2009)). The method is based on complexing in vitro translated proteins of interest to their encoding DNA, which used to determine the sequence of the protein of interest. Typically, a DNA template containing multiple ORFs that can be linked to the protein it encodes is generated. In addition, the coupled transcription/translation reaction is compartmentalized in a water-in-oil emulsion (e.g., micelle).

In some instances, when multiple ORFs are used, they can be separated by ribosomal binding sides. In some embodiments, the coding sequence of the protein of interest is fused to the coding sequence of streptavidin. In some embodiments, the DNA template is biotinylated through a linker. The linker can be cleavable.

During in vitro transcription/translation, the protein can be expressed in a micelle. In one non-limiting illustrative embodiment, the DNA template contains the coding sequence of a $V_H$ chain and/or a $V_L$ chain, and the $V_H$ and $V_L$ chains are expressed in a micelle. In embodiments, a Fab fragment forms and is associated with the DNA encoding the variable chains through a linkage, such as a streptavidin-biotin link. The DNA displayed protein of interest, such as a Fab fragment, can be recovered from the emulsion and screened by affinity selection. The DNA template of the selected DNA-displayed protein of interest can be cleaved from the complex by methods such as UV irradiation and then PCR amplified, cloned, and/or sequenced.

In some embodiments, the methods provided herein include generating a library of nucleic acid members, each member encoding a prospective protein of interest having a primary amino acid different from the other proteins encoded by the other nucleic acid members. In some embodiments, the library comprises DNA members, and the method includes transcribing the library into RNA and translating the RNA in a cell free protein synthesis system to generate a bicistronic DNA display system in a water-in-oil emulsion. In some embodiments, the bicistronic DNA display system contains a population of proteins of interest that are selected for specific binding to a binding pair ligand. In one embodiment, the bicistronic DNA display system contains a population of Fab fragment complexes comprising a $V_H$ chain, in association with a $V_L$ chain, wherein one chain is associated with a DNA molecule encoding the chain. Fab fragments of interest can be selected from the library of Fab fragment complexes.

C. P2A DNA Display

In P2A DNA display, which utilizes the cis-activity of the endonuclease P2A, a fusion protein of P2A and a protein of interest binds to the same DNA molecule from which it is expressed (see, e.g., Reiersen et al., *Nucleic Acids Research*, 33(1): e10). The DNA template can contain the coding sequence encoding the protein of interest genetically fused to the coding sequence of P2A, a promoter, and an origin of replication. The coding sequence of P2A can be obtained and a genetic fusion with the protein of interest can be constructed by standard methods known to those in the art.

In some embodiments, P2A DNA display is used to select a protein of interest. The protein of interest can be selected by generating a library of fusion proteins, where each member of the library comprises a fusion protein between P2A and a protein of interest, and selecting proteins of interest based on a desired property, for example, specific binding to a binding pair ligand. The library can be constructed from a library of nucleic acid members, where each member comprises a DNA template encoding a different protein of interest (i.e., each protein of interest has a primary amino acid sequence that is different from other proteins encoded by other members of the nucleic acid library) that is genetically fused to the coding sequence of P2A.

In some embodiments, the P2A DNA-displayed library can be screened by affinity selection strategies, e.g., in solution or on a solid support. The selected protein of interest can be purified by, e.g., affinity chromatography, and the complexed DNA can be PCR amplified, cloned and/or sequenced.

D. CIS Display

Similar to P2A DNA display, CIS display involves a DNA-based approach to directly link in vitro transcribed/translated proteins to the DNA molecules that encode them (see, e.g., Odegrip et al., *Proc. Natl. Acad. Sci. USA*, 101(9):2806-2810). This method uses RepA, a DNA replication initiator protein, to non-covalently bind to the DNA molecule from which it is expressed if the DNA molecule has a CIS element. The DNA molecule can be created to encode proteins of interest (e.g., VH chains, VL chains, Fab fragments, scFv's) in addition to RepA.

In some embodiments, CIS display is used to select a protein of interest. The protein of interest can be selected by generating a DNA library of fusion proteins, where each member comprises a fusion protein between RepA and a protein of interest, and selecting proteins of interest based on a desired property, for example, specific binding to a binding pair ligand. The library can be constructed from a DNA library, where each member of the library comprises a DNA template encoding a different protein of interest (i.e., each protein of interest has a primary amino acid sequence that is different from other proteins encoded by other members of the nucleic acid library) that is genetically fused to the coding sequence of RepA.

In some embodiments, members of the DNA library contain a coding sequence of the protein of interest, a coding sequence of RepA, a CIS element, an origin of replication and a promoter, wherein the coding sequence of the protein of interest is genetically fused to the coding sequence of RepA. The CIS element can be genetically linked to the RepA coding sequence.

In some embodiments, the library contains a fusion protein between RepA and a protein of interest, and a DNA molecule encoding the fusion protein.

The RepA DNA-displayed library can be screened by affinity selection strategies, e.g., in solution or on a solid support. The selected protein of interest can be purified by, e.g., affinity chromatography, and the complexed DNA can be PCR amplified, cloned and/or sequenced.

III. Cell-Free Protein Synthesis (CFPS)

In order to express the biologically active proteins of interest described herein, a cell free protein synthesis system can be used. Cell extracts have been developed that support the synthesis of proteins in vitro from purified mRNA transcripts or from mRNA transcribed from DNA during the in vitro synthesis reaction.

CFPS of polypeptides in a reaction mix comprises bacterial extracts and/or defined reagents. The reaction mix comprises at least ATP or an energy source; a template for production of the macromolecule, e.g., DNA, mRNA, etc.; amino acids, and such co-factors, enzymes and other reagents that are necessary for polypeptide synthesis, e.g., ribosomes, tRNA, polymerases, transcriptional factors, aminoacyl synthetases, elongation factors, initiation factors, etc. In one embodiment of the invention, the energy source is a homeostatic energy source. Also included may be enzyme(s) that catalyze the regeneration of ATP from high-energy phosphate bonds, e.g., acetate kinase, creatine kinase, etc. Such enzymes may be present in the extracts used for translation, or may be added to the reaction mix. Such synthetic reaction systems are well-known in the art, and have been described in the literature.

The templates for cell-free protein synthesis can be either mRNA or DNA. The template can comprise sequences for any particular gene of interest, and may encode a full-length polypeptide or a fragment of any length thereof. Nucleic acids that serve as protein synthesis templates are optionally derived from a natural source or they can be synthetic or recombinant. For example, DNAs can be recombinant DNAs, e.g., plasmids, viruses or the like.

The term "reaction mix" as used herein, refers to a reaction mixture capable of catalyzing the synthesis of polypeptides from a nucleic acid template. The reaction mixture comprises extracts from bacterial cells, e.g, *E. coli* S30 extracts. S30 extracts are well known in the art, and are described in, e.g., Lesley, S. A., et al. (1991), *J. Biol. Chem.* 266, 2632-8. The synthesis can be performed under either aerobic or anaerobic conditions.

In some embodiments, the bacterial extract is dried. The dried bacterial extract can be reconstituted in milli-Q water (e.g., reverse osmosis water) at 110% of the original solids as determined by measuring the percent solids of the starting material. In one embodiment, an accurately weighed aliquot of dried extract, representing 110% of the original solids of 10 mL of extract, is added to 10 mL of Milli-Q water in a glass beaker with a stir bar on a magnetic stirrer. The resulting mixture is stirred until the powder is dissolved. Once dissolved, the material is transferred to a 15 mL Falcon tube and stored at −80 C unless used immediately.

The volume percent of extract in the reaction mix will vary, where the extract is usually at least about 10% of the total volume; more usually at least about 20%; and in some instances may provide for additional benefit when provided at at least about 50%; or at least about 60%; and usually not more than about 75% of the total volume.

The general system includes a nucleic acid template that encodes a protein of interest. The nucleic acid template is an RNA molecule (e.g., mRNA) or a nucleic acid that encodes an mRNA (e.g., RNA, DNA) and be in any form (e.g., linear, circular, supercoiled, single stranded, double stranded, etc.). Nucleic acid templates guide production of the desired protein.

To maintain the template, cells that are used to produce the extract can be selected for reduction, substantial reduction or elimination of activities of detrimental enzymes or for enzymes with modified activity. Bacterial cells with modified nuclease or phosphatase activity (e.g., with at least one mutated phosphatase or nuclease gene or combinations thereof) can be used for synthesis of cell extracts to increase synthesis efficiency. For example, an *E. coli* strain used to make an S30 extract for CFPS can be RNase E or RNase A deficient (for example, by mutation).

CFPS systems can also be engineered to guide the incorporation of detectably labeled amino acids, or unconventional or unnatural amino acids, into a desired protein. The amino acids can be synthetic or derived from another biological source. Various kinds of unnatural amino acids, including without limitation detectably labeled amino acids, can be added to CFPS reactions and efficiently incorporated into proteins for specific purposes. See, for example, Albayrak, C. and Swartz, J R., *Biochem. Biophys Res. Commun.*, 431(2):291-5; Yang W C et al., *Biotechnol. Prog.* (2012), 28(2):413-20; Kuechenreuther et al, *PLoS One*, (2012), 7(9):e45850; and Swartz J R., *AIChE Journal*, 58(1):5-13.

In a generic CFPS reaction, a gene encoding a protein of interest is expressed in a transcription buffer, resulting in mRNA that is translated into the protein of interest in a CFPS extract and a translation buffer. The transcription buffer, cell-free extract and translation buffer can be added separately, or two or more of these solutions can be combined before their addition, or added contemporaneously.

To synthesize a protein of interest in vitro, a CFPS extract at some point comprises a mRNA molecule that encodes the protein of interest. In some CFPS systems, mRNA is added exogenously after being purified from natural sources or prepared synthetically in vitro from cloned DNA using RNA polymerases such as RNA polymerase II, SP6 RNA polymerase, T3 RNA polymerase, T7 RNA polymerase, RNA polymerase III and/or phage derived RNA polymerases. In other systems, the mRNA is produced in vitro from a template DNA; both transcription and translation occur in this type of CFPS reaction. In some embodiments, the transcription and translation systems are coupled or comprise complementary transcription and translation systems, which carry out the synthesis of both RNA and protein in the same reaction. In such in vitro transcription and translation systems, the CFPS extracts contain all the components (exogenous or endogenous) necessary both for transcription (to produce mRNA) and for translation (to synthesize protein) in a single system.

A cell free protein synthesis reaction mixture comprises the following components: a template nucleic acid, such as DNA, that comprises a gene of interest operably linked to at least one promoter and, optionally, one or more other regulatory sequences (e.g., a cloning or expression vector containing the gene of interest) or a PCR fragment; an RNA polymerase that recognizes the promoter(s) to which the gene of interest is operably linked and, optionally, one or more transcription factors directed to an optional regulatory sequence to which the template nucleic acid is operably linked; ribonucleotide triphosphates (rNTPs); optionally, other transcription factors and co-factors therefor; ribosomes; transfer RNA (tRNA); other or optional translation factors (e.g., translation initiation, elongation and termination factors) and co-factors therefore; one or more energy sources, (e.g., ATP, GTP); optionally, one or more energy regenerating components (e.g., PEP/pyruvate kinase, AP/acetate kinase or creatine phosphate/creatine kinase); optionally factors that enhance yield and/or efficiency (e.g., nucleases, nuclease inhibitors, protein stabilizers, chaperones) and co-factors therefore; and; optionally, solubilizing agents. The reaction mix further comprises amino acids and other materials specifically required for protein synthesis, including salts (e.g., potassium, magnesium, ammonium, and manganese salts of acetic acid, glutamic acid, or sulfuric acids), polymeric compounds (e.g., polyethylene glycol, dextran, diethyl aminoethyl dextran, quaternary aminoethyl and aminoethyl dextran, etc.), cyclic AMP, inhibitors of protein or nucleic acid degrading enzymes, inhibitors or regulators of protein synthesis, oxidation/reduction adjuster (e.g., DTT, ascorbic acid, glutathione, and/or their oxides), non-denaturing surfactants (e.g., Triton X-100), buffer components, spermine, spermidine, putrescine, etc. Components of CFPS reactions are discussed in more detail in U.S. Pat. Nos. 7,338,789 and 7,351,563, and U.S. App. Pub. No. 2010/0184135, the disclosures of which are incorporated by reference in its entirety for all purposes.

Depending on the specific enzymes present in the extract, for example, one or more of the many known nuclease, polymerase or phosphatase inhibitors can be selected and advantageously used to improve synthesis efficiency.

Protein and nucleic acid synthesis typically requires an energy source. Energy is required for initiation of transcription to produce mRNA (e.g., when a DNA template is used and for initiation of translation high energy phosphate for example in the form of GTP is used). Each subsequent step of one codon by the ribosome (three nucleotides; one amino acid) requires hydrolysis of an additional GTP to GDP. ATP is also typically required. For an amino acid to be polymerized during protein synthesis, it must first be activated. Significant quantities of energy from high energy phosphate bonds are thus required for protein and/or nucleic acid synthesis to proceed.

An energy source is a chemical substrate that can be enzymatically processed to provide energy to achieve desired chemical reactions. Energy sources that allow release of energy for synthesis by cleavage of high-energy phosphate bonds such as those found in nucleoside triphosphates, e.g., ATP, are commonly used. Any source convertible to high energy phosphate bonds is especially suitable. ATP, GTP, and other triphosphates can normally be considered as equivalent energy sources for supporting protein synthesis.

To provide energy for the synthesis reaction, the system can include added energy sources, such as glucose, pyruvate, phosphoenolpyruvate (PEP), carbamoyl phosphate, acetyl phosphate, creatine phosphate, phosphopyruvate, glyceraldehyde-3-phosphate, 3-Phosphoglycerate and glucose-6-phosphate, that can generate or regenerate high-energy triphosphate compounds such as ATP, GTP, other NTPs, etc.

When sufficient energy is not initially present in the synthesis system, an additional source of energy is preferably supplemented. Energy sources can also be added or supplemented during the in vitro synthesis reaction.

In some embodiments, the cell-free protein synthesis reaction is performed using the PANOx-SP system comprising NTPs, *E. coli* tRNA, amino acids, $Mg^{2+}$ acetate, $Mg^{2+}$ glutamate, $K^+$ acetate, $K^+$ glutamate, folinic acid, Tris pH 8.2, DTT, pyruvate kinase, T7 RNA polymerase, disulfide isomerase, phosphoenol pyruvate (PEP), NAD, CoA, Na+ oxalate, putrescine, spermidine, and S30 extract.

In some instances, the cell-free synthesis reaction does not require the addition of commonly secondary energy sources, yet uses co-activation of oxidative phosphorylation and protein synthesis. In some instances, CFPS is performed in a reaction such as the Cytomim (cytoplasm mimic) system. The Cytomim system is defined as a reaction condition performed in the absence of polyethylene glycol with optimized magnesium concentration. This system does not accumulate phosphate, which is known to inhibit protein synthesis.

The presence of an active oxidative phosphorylation pathway can be tested using inhibitors that specifically inhibit the steps in the pathway, such as electron transport chain inhibitors. Examples of inhibitors of the oxidative phosphorylation pathway include toxins such as cyanide, carbon monoxide, azide, carbonyl cyanide m-chlorophenyl hydrazone (CCCP), and 2,4-dinitrophenol, antibiotics such as oligomycin, pesticides such as rotenone, and competitive inhibitors of succinate dehydrogenase such as malonate and oxaloacetate.

In some embodiments, the cell-free protein synthesis reaction is performed using the Cytomim system comprising NTPs, E. coli tRNA, amino acids, $Mg^{2+}$ acetate, $Mg^{2+}$ glutamate, $K^+$ acetate, $K^+$ glutamate, folinic acid, Tris pH 8.2, DTT, pyruvate kinase, T7 RNA polymerase, disulfide isomerase, sodium pyruvate, NAD, CoA, Na+ oxalate, putrescine, spermidine, and S30 extract. In some embodiments, the energy substrate for the Cytomim system is pyruvate, glutamic acid, and/or glucose. In some embodiments of the system, the nucleoside triphosphates (NTPs) are replaced with nucleoside monophosphates (NMPs).

The cell extract can be treated with iodoacetamide in order to inactivate enzymes that can reduce disulfide bonds and impair proper protein folding. In some embodiments, the cell extract comprises an exogenous protein chaperone. The protein chaperone can be expressed by the bacterial strain used to make the cell free extract, or the protein chaperone can be added to the cell extract. Non-limiting examples of exogenous protein chaperones include disulfide bond isomerase (PDI), such as, but not limited to E. coli DsbC, and peptidyl prolyl cis-trans isomerase (PPIase), such as but not limited to FkpA. In some embodiments, the extract comprises both a PDI and a PPIase, e.g., both DsbC and FkpA. Glutathione disulfide (GSSG) and/or glutathione (GSH) can also be added to the extract at a ratio that promotes proper protein folding and prevents the formation of aberrant protein disulfides.

In some embodiments, the CFPS reaction includes inverted membrane vesicles to perform oxidative phosphorylation. These vesicles can be formed during the high pressure homogenization step of the preparation of cell extract process, as described herein, and remain in the extract used in the reaction mix.

Methods of preparing a cell extract are described in, e.g., Zawada, J. "Preparation and Testing of E. coli S30 In Vitro Transcription Translation Extracts", Douthwaite, J. A. and Jackson, R. H. (eds.), Ribosome Display and Related Technologies: Methods and Protocols, Methods in Molecular Biology, vol. 805, pp. 31-41 (Humana Press, 2012); Jewett et al., Molecular Systems Biology: 4, 1-10 (2008); Shin J. and Norieaux V., J. Biol. Eng., 4:8 (2010). Briefly, a bacterial culture is grown and harvested; suspended in an appropriate buffer (e.g., S30 buffer), and homogenized to lyse the cells.

The cell-free extract can be thawed to room temperature before use in the CFPS reaction. The extract can be incubated with 50 µM iodoacetamide for 30 minutes when synthesizing protein with disulfide bonds. In some embodiments, the CFPS reaction includes about 30% (v/v) iodoacetamide-treated extract with about 8 mM magnesium glutamate, about 10 mM ammonium glutamate, about 130 mM potassium glutamate, about 35 mM sodium pyruvate, about 1.2 mM AMP, about 0.86 mM each of GMP, UMP, and CMP, about 2 mM amino acids (about 1 mM for tyrosine), about 4 mM sodium oxalate, about 0.5 mM putrescine, about 1.5 mM spermidine, about 16.7 mM potassium phosphate, about 100 mM T7 RNA polymerase, about 2-10 µg/mL plasmid DNA template, about 1-10 µM E. coli DsbC, and a total concentration of about 2 mM oxidized (GSSG) glutathione. Optionally, the cell free extract can include 1 mM of reduced (GSH).

The cell free synthesis reaction conditions may be performed as batch, continuous flow, or semi-continuous flow, as known in the art. The reaction conditions are linearly scalable, for example, the 0.3 L scale in a 0.5 L stirred tank reactor, to the 4 L scale in a 10 L fermentor, and to the 100 L scale in a 200 L fermentor.

The development of a continuous flow in vitro protein synthesis system by Spirin et al. (1988) Science 242:1162-1164 proved that the reaction could be extended up to several hours. Since then, numerous groups have reproduced and improved this system (see, e.g., Kigawa et al. (1991) J. Biochem. 110:166-168; Endo et al. (1992) J. Biotechnol. 25:221-230). Kim and Choi (Biotechnol. Prog. 12: 645-649, 1996) have reported that the merits of batch and continuous flow systems can be combined by adopting a "semicontinuous operation" using a simple dialysis membrane reactor. They were able to reproduce the extended reaction period of the continuous flow system while maintaining the initial rate of a conventional batch system. However, both the continuous and semi-continuous approaches require quantities of expensive reagents, which must be increased by a significantly greater factor than the increase in product yield.

Several improvements have been made in the conventional batch system (Kim et al. (1996) Eur. J. Biochem. 239: 881-886; Kuldlicki et al. (1992) Anal. Biochem. 206:389-393; Kawarasaki et al. (1995) Anal. Biochem. 226: 320-324). Although the semicontinuous system maintains the initial rate of protein synthesis over extended periods, the conventional batch system still offers several advantages, e.g. convenience of operation, easy scale-up, lower reagent costs and excellent reproducibility. Also, the batch system can be readily conducted in multiplexed formats to express various genetic materials simultaneously.

Patnaik and Swartz (Biotechniques 24:862-868, 1998) have reported that the initial specific rate of protein synthesis could be enhanced to a level similar to that of in vivo expression through extensive optimization of reaction conditions. It is notable that they achieved such a high rate of protein synthesis using the conventional cell extract prepared without any condensation steps (Nakano et al. (1996) J. Biotechnol. 46:275-282; Kim et al. (1996) Eur. J. Biochem. 239:881-886). Kigawa et al. (1999) FEBS Lett 442: 15-19 report high levels of protein synthesis using condensed extracts and creatine phosphate as an energy source. These results imply that further improvement of the batch system, especially in terms of the longevity of the protein synthesis reaction, would substantially increase the productivity for batch in vitro protein synthesis. However, the reason for the early halt of protein synthesis in the conventional batch system has remained unclear.

The protein synthesis reactions described herein can utilize a large scale reactor, small scale, or may be multiplexed to perform a plurality of simultaneous syntheses. Continuous reactions can use a feed mechanism to introduce a flow of reagents, and may isolate the end-product as part of the process. Batch systems are also of interest, where additional reagents may be introduced to prolong the period of time for active synthesis. A reactor can be run in any mode such as batch, extended batch, semi-batch, semi-continuous, fed-batch and continuous, and which will be selected in accordance with the application purpose.

A. Generating a Lysate

The methods and systems described herein can use a cell lysate for in vitro translation of a target protein of interest. For convenience, the organism used as a source for the lysate may be referred to as the source organism or host cell. Host cells may be bacteria, yeast, mammalian or plant cells, or any other type of cell capable of protein synthesis. A lysate comprises components that are capable of translating messenger ribonucleic acid (mRNA) encoding a desired protein, and optionally comprises components that are capable of transcribing DNA encoding a desired protein. Such components include, for example, DNA-directed RNA polymerase (RNA polymerase), any transcription activators that are required for initiation of transcription of DNA encoding the desired protein, transfer ribonucleic acids (tRNAs), amino-acyl-tRNA synthetases, 70S ribosomes, $N^{10}$-formyltetrahydrofolate, formylmethionine-tRNAf$^{Met}$ synthetase, peptidyl transferase, initiation factors such as IF-1, IF-2, and IF-3, elongation factors such as EF-Tu, EF-Ts, and EF-G, release factors such as RF-1, RF-2, and RF-3, and the like.

An embodiment uses a bacterial cell from which a lysate is derived. A bacterial lysate derived from any strain of bacteria can be used in the methods of the invention. The bacterial lysate can be obtained as follows. The bacteria of choice are grown to log phase in any of a number of growth media and under growth conditions that are well known in the art and easily optimized by a practitioner for growth of the particular bacteria. For example, a natural environment for synthesis utilizes cell lysates derived from bacterial cells grown in medium containing glucose and phosphate, where the glucose is present at a concentration of at least about 0.25% (weight/volume), more usually at least about 1%; and usually not more than about 4%, more usually not more than about 2%. An example of such media is 2YTPG medium, however one of skill in the art will appreciate that many culture media can be adapted for this purpose, as there are many published media suitable for the growth of bacteria such as E. coli, using both defined and undefined sources of nutrients. Cells that have been harvested overnight can be lysed by suspending the cell pellet in a suitable cell suspension buffer, and disrupting the suspended cells by sonication, breaking the suspended cells in a French press, continuous flow high pressure homogenization, or any other method known in the art useful for efficient cell lysis The cell lysate is then centrifuged or filtered to remove large DNA fragments and cell debris.

The bacterial strain used to make the cell lysate generally has reduced nuclease and/or phosphatase activity to increase cell free synthesis efficiency. For example, the bacterial strain used to make the cell free extract can have mutations in the genes encoding the nucleases RNase E and RNase A. The strain may also have mutations to stabilize components of the cell synthesis reaction such as deletions in genes such as tnaA, speA, sdaA or gshA, which prevent degradation of the amino acids tryptophan, arginine, serine and cysteine, respectively, in a cell-free synthesis reaction. Additionally, the strain may have mutations to stabilize the protein products of cell-free synthesis such as knockouts in the proteases ompT or lonP.

IV. Proteins of Interest

The methods and systems described herein are useful for stabilizing the nucleic acid template (e.g., mRNA) encoding a protein of interest, and for selecting improved versions of the protein of interest. The protein of interest can be any protein that is capable of being expressed in a bacterial cell free synthesis system. Non-limiting examples of such proteins of interest include antibodies or fragments thereof, single chain antibodies, therapeutic proteins, growth factors, receptors, hormones, cytokines, enzymes, ligands, and viral proteins. Other proteins of interest include proteins with disulfide bonds and proteins with at least two proline residues. In some embodiments, the protein of interest is a $V_H$ chain, a $V_L$ chain, a Fab fragment, or an scFv.

V. DNA Expression Cassette without Stop Codon

In some embodiments, the nucleic acid template used in the ribosomal display reaction system comprises a DNA expression cassette that is capable of expressing an RNA encoding the protein of interest, where the RNA lacks an operable stop codon. To remove the stop codon from the protein coding region in the expression cassette, a PCR primer lacking the stop codon can be used to amplify the coding region for the protein of interest, such that the entire coding region from the translation start to the sequence encoding the C-terminal amino acid is amplified.

VI. Lambda Gam Protein

λGam (gamma) protein is a host-nuclease inhibitor that acts on host bacteria. During phage rolling circle replication, Gam prevents host bacterial RecBCD nuclease from degrading the 3' ends of viral linear double-stranded DNA (dsDNA), such as the replication intermediates generated in the lytic cycle of phage λ (see, e.g., Friedman S A and Hays, J B., Gene, 43(3):255-263 (1986)).

Two different forms of λGam protein, Gam L and Gam S, have been identified. GamL protein is about 138 amino acids long and has a predicted molecular weight of 16.1 kDa. Gam S protein is about 98 amino acids long and has a predicted molecular weight of 11.6 kDa. Both λGamL and λGamS are encoded by the lambda gam (gamma) gene (Gene ID: 2703509), produced after splicing of the transcript to generate GamL or GamS, and processed to produce the polypeptide of Gam L (GenBank Accession No. NP_040618; Weigel, P. H., et a, Proc. Natl. Acad. Sci. U.S.A. 70(4):1151-1155, 1973) or GamS (GenBank Accession No. YP_002928890; Ferenci, T., et al., J. Bacteriol. 191(12): 4025-4029, 2009). The coding sequences of GamL and GamS share the same reading frame and translational stop. There are multiple variants in the amino acid sequence of lambda Gam, examples of which may be found in the BLASTp function using GenBank Accession No. NP_040618 for GamL, or GenBank Accession No. YP_002928890 for GamS.

It will be understood that Gam protein of bacteriophage lambda described herein shares high sequence similarity and identity to a number of Gam proteins of other bacteriophages or bacteria (e.g., phage Mu, phage VT2-Sakai, phage Sf1, Escherichia coli BW2952, Escherichia coli TW07793, Escherichia albertii TW11588, etc.). In some embodiments, Gam genes and proteins of bacteriophages other than lambda can be used in the method provided herein. In some embodiments, the Gam protein is substantially similar to SEQ ID NO:1. In some embodiments, the Gam protein comprises SEQ ID NO:1.

In some embodiments, the Gam protein comprises conservative and/or other amino acid substitutions that do not substantially alter the function of Gam protein. For example, in some embodiments, the Gam protein comprises one or more amino acid substitutions that increase or further increase the stability of an RNA template in a cell free translation system, or comprises amino acid substitutions that do not decrease the stability of an RNA template in a cell free translation system, as compared to a control, unmodified or prototype (reference or wild-type) Gam protein. Examples of amino acid substitutions include N to S at position 2 (N2>S), A3>T, Y4>W or C, Y5>L or P, Q7>P, R9>C, L10>I, E11>K, A12>E, 14S>A, 16A>T or S, 20Q>R, 21Q>K, 22L>I, A23>V or T, 27K>T or N, 29A>T, 33D>E, 34D>N, 35M>L, I39>L, 51H>Q, N or S, 55H>C, 60K>Q, 61 5>A or T, 63T>I, S, or A, 84V>A, 92V>A or I, and 93D>N or Y, of SEQ ID NO:1.

When the proteins described herein are referred to by name, it is understood that this includes proteins with similar functions and similar amino acid sequences. Thus, the proteins described herein include the wild-type prototype protein, as well as homologs, polymorphic variations and recombinantly created muteins. For example, the name "Gam protein" includes the wild-type prototype protein (e.g., either SEQ ID NO:1 or GenBank Accession No. YP_002928890) from enterobacteria phage lambda, as well as homologs from other species, polymorphic variations and recombinantly created muteins. Gam proteins are defined as having substantially the same biological activity or functional capacity as the wild type protein (e.g., at least 80% of either). Proteins such as Gam are defined as having similar amino acid sequences if they have at least 80%, 85%, 90%, 95%, 96%, 97%, 98%, or 99% sequence identity to the prototype protein. The sequence identity of a protein is determined using the BLASTP program with the defaults wordlength of 3, an expectation (E) of 10, and the BLOSUM62 scoring matrix (see Henikoff and Henikoff, Proc. Natl. Acad. Sci. USA 89:10915-10919, 1992).

A readily conventional test to determine if a protein homolog, polymorphic variant or recombinant mutein is inclusive of a protein described herein is by specific binding to polyclonal antibodies generated against the prototype protein. For example, a Gam protein includes proteins that bind to polyclonal antibodies generated against the prototype protein of SEQ ID NO:1. To determine if polyclonal antibodies bind to a putative Gam protein, the test protein is incubated with polyclonal antibodies under immunoassay conditions sufficient to permit specific binding of the antibodies to the test protein. A protein is defined as a Gam protein if the polyclonal antibodies bind to the test protein at least two times the background, under designated immunoassay conditions, and the polyclonal antibodies do not substantially bind in a significant amount to other proteins present in the sample. For example, polyclonal antibodies raised to Gam, splice variants, or portions thereof, can be selected to obtain only those polyclonal antibodies that are specifically immunoreactive with Gam and not with other proteins, except for polymorphic variants of Gam. This selection may be achieved by subtracting out antibodies that cross-react with other members of the Gam family. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective reaction will be at least twice background signal or noise and more typically more than 10 to 100 times background.

A. Preparation of λGam

The λGam protein can be provided in the ribosomal display reaction system in a variety of forms. In some embodiments, the λGam protein is provided in a cell-free extract, e.g., as obtained from a recombinant protein production or expression system prior to protein purification. For instance, an *E. coli* extract can be generated from a host cell that heterologously expresses a polynucleotide that gives rise to the λGam protein. In other instances, the polynucleotide acid encoding λGam is integrated in the genome of the host cells. Methods for expressing nucleic acids in host cells are routinely practiced by those skilled in the art. For example, routine protocols for introducing and maintaining exogenous polynucleotides in a host cell are described in, e.g., Sambrook et al., MOLECULAR CLONING, A LABORATORY MANUAL, Cold Springs Harbor Press (Cold Springs Harbor, N.Y. 1989).

In other embodiments, the λGam protein is provided as a purified protein. λGam protein can be purified from a host cell that expresses a polynucleotide encoding the protein by various methods known to those skilled in the art. For instance, the host cell can be disrupted (e.g., by mechanical shear, freeze/thaw, osmotic shock, chemical treatment, and/or enzymatic treatment) to generate a cell lysate that contains the λGam protein and other cellular constituents. λGam protein can be separated from the other cellular constituents by e.g., filtration, centrifugation, and chromatography (e.g., affinity chromatography, size exclusion chromatography, ion exchange chromatography). A detailed description of making purified Gam protein is found in, for example, Murphy, K C., J. Bacteriology, 173(18): 5808-5821 (1991).

In another embodiment, λGam proteins can be produced by a coupled transcription/translation system. Such a system contains all the biomolecules needed for transcription and translation. Typically, the method includes adding a polynucleotide encoding λGam protein to a cell lysate or a cell extract that can support transcription and translation.

In another embodiment, λGam proteins can be produced in a cell-free protein synthesis system, as described herein.

In yet another embodiment, λGam proteins can be produced by a cell-free translation system such as the PURE system (see, e.g., Shimizu et al., *Nat. Biotechnol.*, 19:751-755 (2001)). The PURE system can include about 32 individually purified components used for in vitro protein biosynthesis (e.g., initiation, elongation and termination). In some embodiments, the components include initiation factors (e.g., IF1, IF2, IF3), elongation factors (e.g., EF-G, EF-Tu, EF-Ts), release factors (e.g., RF1, RF3), a termination factor (e.g., RRF), 20 aminoacyl-tRNA synthetases, methionyl-tRNA transformylase, T7 RNA polymerase, ribosomes, 46 tRNAs, NTPs, creatine phosphate, 10-formyl-5,6,7,8-tetrahydrofolic acid, 20 amino acids, creatine kinase, myokinase, nucleoside-diphophate kinase and pryophosphatase.

λGam can be purified by separating it from the other components of the system by e.g., filtration, centrifugation, and chromatography (e.g., affinity chromatography, size exclusion chromatography, ion exchange chromatography).

In some embodiments, λGam proteins can be synthesized chemically, such as by solution or solid phase peptide synthesis.

B. λGam in Ribosomal Display Reaction Systems

In some embodiments, λGam protein is present in the ribosomal display reaction system at a final concentration of about 25 to about 80 μg/ml, e.g., 25, 25, 26, 27, 28, 29, 30, 31, 33, 35, 37, 39, 40, 41, 43, 45, 47, 49, 50, 53, 55, 57, 59, 61, 63, 65, 67, 69, 71, 73, 75, 77, 79, or 80 μg/ml. In various embodiments, the λGamS protein is present in the cell-free translation system at a final concentration of about 25 to about 80 μg/ml, e.g., 25, 25, 26, 27, 28, 29, 30, 31, 33, 35, 37, 39, 40, 41, 43, 45, 47, 49, 50, 53, 55, 57, 59, 61, 63, 65, 67, 69, 71, 73, 75, 77, 79, or 80 μg/ml. In other embodiments, λGam protein is present in the ribosomal display reaction system at a final concentration of about 25 to about 60 μg/ml, e.g., 25, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 μg/ml. In some embodiments, the λGamS protein is present in the cell-free translation system at a final concentration of about 25 to about 60 μg/ml, e.g., 25, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 μg/ml.

C. Determining the Stability of the RNA Template in Extracts Comprising λGam

The inventors have discovered that the addition of Gam protein to the coupled transcription-translation reaction increases the stability of the RNA transcript in the complexes formed in the ribosomal display reaction system (RDRS). This provides the advantage of displaying more protein for longer than in previous methods. The term "increases the stability of the RNA" refers to an increase in the effective amount of the RNA-containing complexes in the display reaction system as compared to the effective amount of complexes in a control reaction system in the absence of λGam. While not being bound by any particular theory or mechanism of action, the addition of Gam protein to the reaction could increase the stability of the RNA transcript by preventing degradation of the RNA, either directly or indirectly. Alternatively, the addition of Gam protein to the reaction could increase the stability of the RNA transcript by preventing degradation of the DNA template that is used for in vitro transcription, thereby effectively increasing the amount of DNA template, which could lead to an increase in the amount of RNA transcribed from the DNA template.

As described in the Examples, the stability of the mRNA transcript can be determined by converting the mRNA to double stranded DNA by RT-PCR at various time points after starting the reaction, and quantifying the amount of DNA present at each time point. For example, recovery of mRNA from the complex at 15, 30, 45 and 60 minutes was greater than 5-fold higher when Gam was present as compared to complexes incubated in the absence of Gam protein. In the absence of λGam protein, the mRNA appeared to noticeably degrade after 45 minutes of incubation at 30° C., but appears to be stable up to at least 60 minutes in the presence of GamS. In some embodiments, the RDRS is performed at 30° C. in the presence of Gam for about 10 to about 90 minutes, e.g., 10, 15, 20, 25, 30, 35, 40, 45, 50, 55, 60, 65, 70, 75, 80, 85, or 90 minutes.

EXAMPLES

Example 1

This example describes the selection of scFv and Fabs using multiple rounds of selection in the ribosomal display reaction system described herein, and shows that inclusion of Gam protein in the RDRS improves the stability of the mRNA template in the coupled transcription-translation reaction complexes.

A. Library Design for scFv and Fabs (Heavy Chain Only and Heavy+Light Diversity)

The Fab HC library was built onto the trastuzumab Fab HC scaffold. The trastuzumab scaffold was cloned into the NcoI and HindIII sites of a pUC ribosome display vector containing the TolA spacer (same insert as pRDV, GenBank AY327136.1). The Fab HC only library design was based on the published library (Lee et al, JMB 2004, 340, 1073-1093) using the same limited diversity in CDRs H1 and H2. CDR H3 was restricted to a single loop length of 11 amino acids and 8 residues were randomized using NNK codons. The library was constructed using overlapping PCR as below.

For the Fab HC library, synthetic oligonucleotides (Table 1) containing degenerate codons were dissolved to give 100 μM stocks. T7B and TolAk primers have been previously reported (Dreier and Plückthun, *Methods Mol. Biol.* 2011 687, 283-306). Primer sets were mixed to give similar degeneracy as Lee et al. H1a For and H1b For were mixed at a 2:1 ratio to give H1 For mix; H2a For, H2b For, and H2c For were mixed at a ratio of 1:2:0.1 to give H2 For mix; and H3a For and H3a For were mixed at a ratio of 1:1 to give H3 For mix. The complementary reverse primer sets were mixed separately at the same ratios. Four sets of PCR reactions were performed using (1) T7B/H1 Rev mix, (2) H1 For mix/H2 Rev mix, (3) H2 For mix/H3 Rev mix, and (4) H3F mix and Univ TolA RP. PCR was performed using 10 ng of the wild-type Fab HC ribosome display template and 0.5 μL of 100 μM primer stocks (~3×10$^{13}$ molecules) using 2×HF Phusion polymerase master mix (NEB). The fragments were gel purified and mixed at equimolar ratios (~3.7×10$^{12}$ molecules each) for overlapping PCR (18×50 μL reactions). The assembled library was then amplified using T7B/TolAk primers (48×50 μL reactions) which was then purified and concentrated using Zymo Research DNA Clean and Concentrator spin columns.

The scFv library was built onto the trastuzumab scFv VL-VH scaffold. The VL-VH scFv was cloned in the NcoI and HindIII sites of a pUC ribosome display vector containing the TolA spacer (same insert as pRDV, GenBank AY327136.1). The scFv VH library design was based on the published library (Lee et al, JMB 2004, 340, 1073-1093) using the same limited diversity in CDRs H1 and H2. CDR H3 was restricted to a single loop length of 11 amino acids and 8 residues were randomized using NNK codons. The library was constructed using overlapping PCR as below.

For the scFv VH library, synthetic oligonucleotides (Table 3) containing degenerate codons were dissolved to give 100 μM stocks. Ten nanograms of template plasmid was amplified by PCR (98° C.×30 sec denaturation, 20 cycles of 98° C.×30 sec, 50° C.×15 sec, 72° C.×15 sec per kb, followed by a final extension of 72° C.×30 sec) with 50 picomoles of forward and reverse oligonucleotides using Phusion HF Master Mix (New England Biolabs # M0531L) to create four overlapping, degenerate fragments for the scFv. Two 50 μL PCR reactions were done per scFv fragment. CDRs H1, H2, and H3 were randomized using mixtures of two, three, and two degenerate oligonucleotides, respectively. See Table 2 for primer sequences. Fragment one was amplified with the T7F and a 2:1 ratio of H1aR:H1bR. Fragment two was amplified with a 2:1 ratio of H1aF:H1bF and a 1:2:0.1 ratio of H2aR:H2bR:H2cR. Fragment three was amplified with a 1:2:0.1 ratio of H2aF:H2bF:H2cF and a 1:1 ratio of H3aR: H3aR. Fragment four was amplified with a 1:1 ratio of H3aF:H3aF and TolAR. TolAR anneals to the same place in the TolA spacer as the To1AkR primer but lacks the stem loop hairpin used to increase mRNA stability in ribosome display, allowing for better assembly. The four fragments were gel purified with QIAquick Gel Extraction kit (Qiagen #28706) and 3 picomoles of each fragment were mixed and extended by PCR (95° C.×4 min, ten cycles of 95° C.×20 sec, 55° C.×20 sec, 72° C.×15 sec, followed by a final extension of 72° C.×2 min) in the absence of primers using Phusion GC Master Mix (New England Biolabs # M0532L) with 3% DMSO in 18×50 µL reactions. The extension reaction was used directly for further amplification of the full-length ribosome display cassette by PCR (98° C.×30 sec denaturation, 20 cycles of 98° C.×30 sec, 50° C.×15 sec, 72° C.×15 sec per kb, followed by a final extension of 72° C.×30 sec) with 10 picomoles of the T7F and To1AkR outer primers per 50 µL reaction to add the 3' stem loop hairpin using Phusion GC Master Mix with 3% DMSO. A total of 48×50 µL reactions were run. Reactions were cleaned up with DNA Clean and Concentrator spin columns (Zymo Research # D4034) and PCR product was sequenced (Elimbio) to assess library quality.

B. Selection of scFv in Extract

An aliquot of an scFv library was purified by gel extraction from a 1% agarose gel before the selection. The first round of selection was performing using coupled transcription/translation reactions (8×25 µL each) using ~240 ng of the DNA library (~$10^{12}$ molecules). For subsequent rounds only 2 reactions were performed for the +Ag (25 µL each) and 2 reactions for the −Ag (25 µL each) using between 130-250 ng DNA for each reaction. Coupled transcription/translation were run adding 3 µL of the purified library to 22 µL of cell-free mix supplemented with DsbC, PDI, GSSG, GamS, and an antisense ssrA oligo (Hanes and Pluckthun PNAS 1997, 94, 4937-4942, U.S. Pat. No. 6,589,741 B2; Date: Jul. 8, 2003). The reactions were allowed to proceed for 60 min at 30° C. before quenching. scFvs specific for the Ag were isolated using previously biotinylated Ag (biotinylated using standard protocols). RT-PCR was performed to isolate the coding sequence of scFvs using a 1-step Transcriptor RT-PCR kit (Roche) with primers specific to the scFv library scaffold. The remaining selection was performed using standard protocols (Dreier and Plückthun, *Methods Mol. Biol.* 2011 687, 283-306). Six rounds of selection were performed until the recovery was greater +Ag versus −Ag as assessed by RT-PCR.

C. Selection of Fabs in Extract

An aliquot of the Fab HC library was purified by gel extraction from a 1% agarose gel before the selection. The first round of selection was performing using coupled transcription/translation reactions (8×25 µL each) were each performed using 7.7 µg pre-purified LC protein and ~240 ng of the DNA library (~2000 ng total or 1.7×$10^{12}$ molecules). For subsequent rounds only 2 reactions were performed for the +Ag (25 µL each) and 2 reactions for the −Ag (25 µL each) using between 130-230 ng DNA for each reaction. Coupled transcription/translation were run adding 3 µL of the purified library to 22 µL of cell-free mix supplemented with pre-purified LC protein, DsbC, PDI, GSSG, GamS, and an antisense ssrA oligo (Hanes and Pluckthun PNAS 1997, 94, 4937-4942, U.S. Pat. No. 6,589,741 B2; Date: Jul. 8, 2003). The reactions were allowed to proceed for 60 min at 30° C. before quenching. Fabs specific for the Ag were isolated using previously biotinylated Ag (biotinylated using standard protocols). RT-PCR was performed to isolate the coding sequence of Fabs using a 1-step Transcriptor RT-PCR kit (Roche) with primers specific to the Fab HC library scaffold. The remaining selection was performed using standard protocols (Dreier and Plückthun, *Methods Mol. Biol.* 2011 687, 283-306). Six rounds of selection were performed until the recovery was greater +Ag versus −Ag as assessed by RT-PCR.

D. Characterization of scFvs Selected Using Extract

After the fifth round of ribosome display selection the mRNA output was amplified and subcloned into the BsaI sites of pYD317-CAB scFv-Fc+2BsaI to create scFv-Fc fusions. Individual clones were miniprepped. Two microliters of miniprep DNA were used to express the scFv-Fcs using cell-free protein synthesis in 30 µL reactions of *E. coli* S30 extract with the addition of 4.83 µM PDI and 650 nM DsbC. Reactions were carried out in 96 well plates (NUNC) at 30° C. for 6 hours with 800 rpm shaking followed by a 4° C. overnight hold. The next day reactions were spun down at 5,000×g for 5 min and the supernatants were diluted 1:10 with phosphate buffered saline (PBS)+0.05% Tween20 (Sigma # P9416) (PBST) and used directly in an ELISA.

Ninety-six well NUNC Maxisorp Immunoplates (VWR #62409-002) were coated with 100 µL/well of 5 pg/mL antigen in PBST at 4° C. overnight. The next day plates were blocked with 2% bovine serum albumin (BSA) (Sigma # B4287-25G)+PBST for 1 hour at 25° C. with shaking. Cell-free reactions which had been diluted 1:10 in PB ST were incubated with the blocked plated for 1 hour at 25° C. with shaking to allow scFv-Fc binding. Plates were washed by hand five times with PBST and incubated with a 1:10,000 dilution of a goat anti-human (Fc-specific)-HRP conjugated secondary antibody (Sigma # A0170) in PBST for 30 min at 25° C. with shaking. Plates were washed by hand five times with PBST and incubated with 1-Step Ultra TMB (Thermo Scientific #34028) to allow color development. Reactions were stopped by the addition of 2M H2SO4 and the absorbance was read at 450 nm on a plate reader. A number of clones showed binding to Ag by ELISA (FIG. 1).

E. Characterization of Fabs Selected Using Extract

Figure 2:
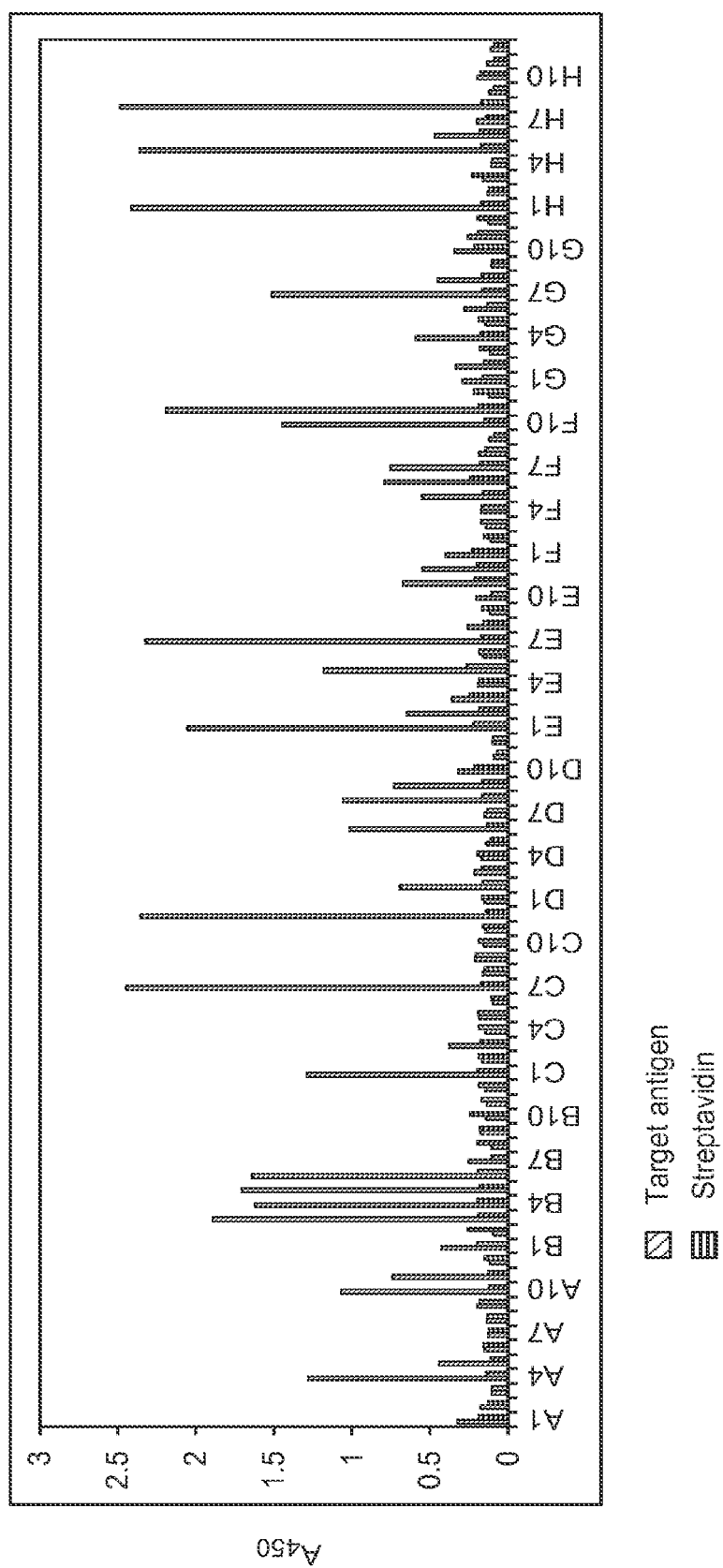
FIG. 2 shows ELISA data of selected Fabs in extract reformatted into IgGs showing specific binding to the target antigen with respect to streptavidin.

Cell-free reactions were run essentially as described previously using DsbC and PDI (Yin, G. et al. mAbs 2012). Small-scale coupled transcription/translation was initiated by addition of 5 µL of non-normalized mini-prepped IgG HC DNA (approximately 50-150 ng/µL) and IgG LC DNA to the cell-free mixture (30 µL final volume) and was incubated at 30° C. for 12 hours in a covered 96-well microtiter plate while shaking at 800 rpm using an Eppendorf Thermomixer R. The crude cell-free reactions were stored at 4° C. until they were centrifuged at 5,000 g for 5 min at 4° C. The supernatant was diluted into 500 µL PBST. A separate MaxiSorp plate was incubated overnight at 4° C. with 100 µL of 5 µg/mL of Ag or streptavidin in PBS. The antigen solution was removed and the plate was blocked with 2% BSA in PBST for 1 hour at room temperature while shaking (500 rpm). Then 100 µL of the diluted crude cell-free reactions were added to the wells and incubated at room temperate for 1 hour with shaking. The plate was washed 5 times with PBST and 100 µL of 1:10,000 dilution of anti-human IgG (Fc specific)-peroxidase antibody conjugate (Sigma) in PBST was incubated for 1 hour at room temperature with shaking. The plate was washed 5 times with PBST and developed with 100 µL TMB for 16 min before quenching with 100 µL 1 N sulfuric acid. Absorbances were measured using a SpectraMax plate reader. FIG. 2 shows examples of Ag specific IgGs reformatted from selected Fabs.

F. GamS Increases Message Stability

Figure 3:
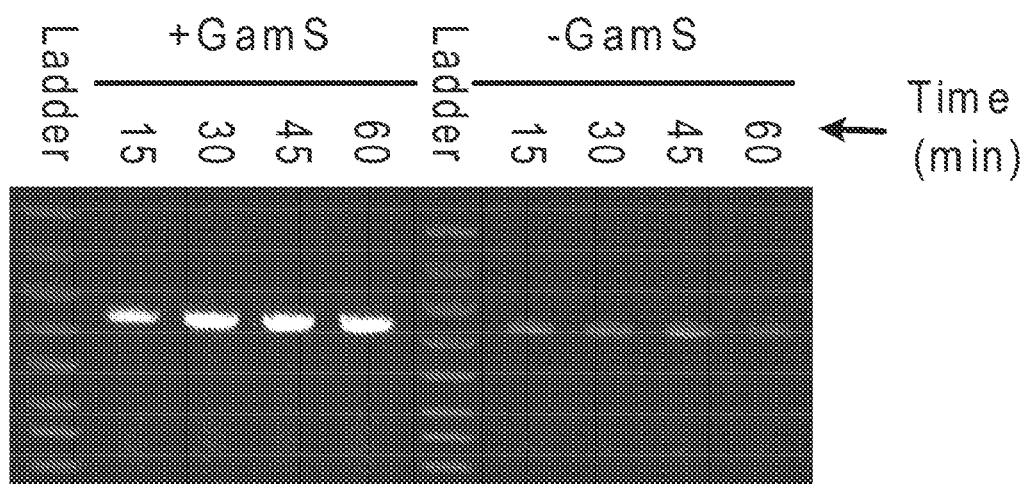
FIG. 3 shows GamS increases the stability of mRNA in extract throughout the coupled transcription/translation reaction at 30° C.
Figure 4:
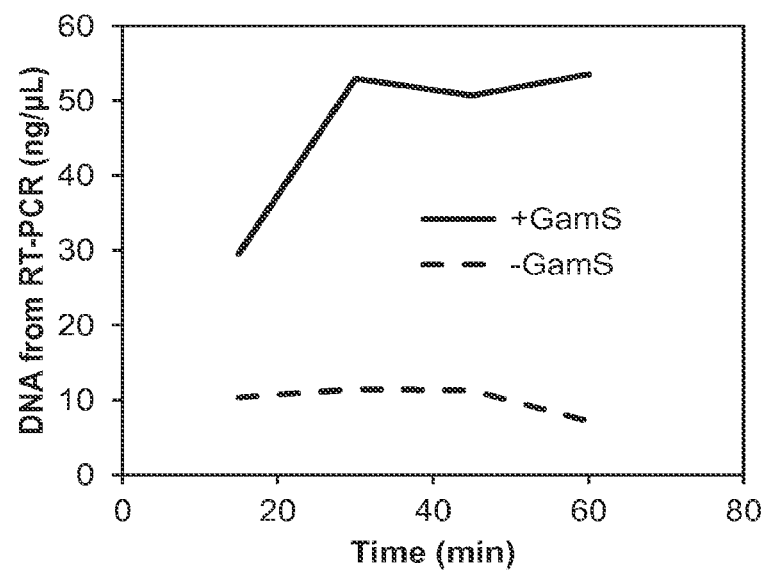
FIG. 4 shows GamS increases the stability and recovery of mRNA during coupled transcription/translation at 30° C. Recoveries of mRNA are >5-fold higher in the presence of GamS. The mRNA appears to degrade after 45 minutes in the absence of GamS, but appears to be stable up to 60 minutes in the presence of GamS.

An anti-CEA scFV and an anti-IL23 scFv were cloned into the pUC ribosome display vector containing the TolA spacer (same insert as pRDV, GenBank AY327136.1). The resulting plasmids were mixed at a 1:1 ratio and amplified using T7B and To1Ak primers (Dreier and Plückthun, *Methods Mol. Biol.* 2011 687, 283-306) to generate linear dsDNA templates. The 1:1 dsDNA mixture was added to cell-free reactions supplemented with DsbC, PDI, GSSG, and an antisense ssrA oligo (Hanes and Pluckthun PNAS 1997, 94, 4937-4942, U.S. Pat. No. 6,589,741 B2; Date: Jul. 8, 2003). Coupled transcription translation using cell-free mixture was performed with or without 36 μg/mL GamS (final concentration) and quenched after 15, 30, 45, and 60 mins. The CEA specific scFv was pulled down from the extract using biotinylated CEA (biotinylated using standard protocols). The remaining selection was performed using standard protocols (Dreier and Plückthun, *Methods Mol. Biol.* 2011 687, 283-306). The recovered mRNA was converted to double-stranded DNA using Transcriptor 1-step RT-PCR kit. Qualitative relative yields were visualized on an agarose gel (FIG. 3). Yields were quantified by UV after purification using a standard DNA purification spin column (FIG. 4). GamS improves recovery over 5-fold at every time-point. The mRNA recovery also appears to be stable up to 60-min in the presence of GamS where mRNA recovery in the absence of GamS appears to fall.

TABLE 1

Primers for Fab HC library construction

| Name | Sequence (5' to 3') (SEQ ID NO:) |
|---|---|
| H1a For | CgcggcaagcggttttaacattAVTRRTWMYKMTatccactgggtgcgtcaagcac (SEQ ID NO: 4) |
| H1a Rev | gtgcttgacgcacccagtggatAKMRKWAYYABTaatgtaaaaccgcttgccgcg (SEQ ID NO: 5) |
| H1b For | cgcggcaagcggttttaacattAVTRRTWMYKGGatccactgggtgcgtcaagcac (SEQ ID NO: 6) |
| H1b Rev | gtgcttgacgcacccagtggatCCMRKWAYYABTaatgtaaaaccgcttgccgcg (SEQ ID NO: 7) |
| H2a For | gggtaagggcctggaatgggttGSTDGGattDMTccgDMTRRCggtDMTaccDACtatgcggatagcgtgaaaggcc (SEQ ID NO: 8) |
| H2a Rev | ggcctttcacgctatccgcataGTHggtAKHaccGYYAKHcggAKHaatCCHASCaacccattccaggcccttaccc (SEQ ID NO: 9) |
| H2b For | gggtaagggcctggaatgggttGSTDHTattDMTccgDMTRRCggtDMTaccDACtatgcggatagcgtgaaaggcc (SEQ ID NO: 10) |
| H2b Rev | ggcctttcacgctatccgcataGTHggtAKHaccGYYAKHcggAKHaatADHASCaacccattccaggcccttaccc (SEQ ID NO: 11) |
| H2c For | gggtaagggcctggaatgggttGSTGAAattDMTccgDMTRRCggtDMTaccDACtatgcggatagcgtgaaaggcc (SEQ ID NO: 12) |
| H2c Rev | ggcctttcacgctatccgcataGTHggtAKHaccGYYAKHcggAKHaatTTCASCaacccattccaggcccttaccc (SEQ ID NO: 13) |
| H3a For | gcagaggacactgccgtctactattgtGCGcgcNNKNNKNNKNNKNNKNNKNNKNNKNNKatgactactggggccaggtac (SEQ ID NO: 14) |
| H3a Rev | gtaccctggccccagtagtccatMNNMNNMNNMNNMNNMNNMNNMNNMNNgcgCGCacaatagtagacggcagtgtcctctgc (SEQ ID NO: 15) |
| H3b For | gcagaggacactgccgtctactattgtGCGcgcNNKNNKNNKNNKNNKNNKNNKNNKTTTgactactggggccaggtacgc (SEQ ID NO: 16) |
| H3b Rev | gcgtaccctggccccagtagtcAAAMNNMNNMNNMNNMNNMNNMNNMNNgcgCGCacaatagtagacggcagtgtcctctgc (SEQ ID NO: 17) |

TABLE 2

Primers for PCR and RT-PCR*

| Name | Sequence (5' to 3') (SEQ ID NO:) |
|---|---|
| HER2_FAB_HC_STOP!RP | TTA TTA ACA ACA AGA TTT CGG CTC CAC CT (SEQ ID NO: 18) |
| HER2_FAB_LC_STOP!RP | TTA TTA GCA CTC ACC GCG GTT AAA (SEQ ID NO: 19) |
| FAB FP | ATG GAA GTT CAA TTA GTA GAA AGC GGC G (SEQ ID NO: 20) |
| FAB RP | ACA AGA TTT CGG CTC CAC CTT CTT G (SEQ ID NO: 21) |
| Fc FP | CAA GAA GGT GGA GCC GAA ATC TTG T (SEQ ID NO: 22) |
| Fc RP | CTT ACC CGG GGA CAG GGA CAA G (SEQ ID NO: 23) |
| HC FP | TAT ACA TAT GGA AGT TCA ATT AGT AGA AAG CGG CG (SEQ ID NO: 24) |
| HC RP | TTT TGT CGA CCT TAC CCG GGG ACA GGG ACA AG (SEQ ID NO: 25) |
| Univ TolA RP | TTC AGT TGC CGC TTT CTT TC (SEQ ID NO: 26) |
| HER2 HCFAB Inner FP | GAG ATA TAT CCA TGG AAG TTC AAT TAG TAG AAA GC (SEQ ID NO: 27) |
| HER2 HCFAB Inner RP | GAG GCG ATA TAA AGC TTA CAA GAT TTC GG (SEQ ID NO: 28) |
| TolA Internal RP | CTT TGG CGG CTT CTG CTT (SEQ ID NO: 29) |

*T7B and TolAk primers have been previously reported by Dreier and Plückthun, *Methods Mol. Biol.* 687, 283-306, (2011).

TABLE 3

Primers for scFv VH library construction

| Primer | Sequence (5' to 3') (SEQ ID NO:) |
|---|---|
| T7F | atacgaaattaatacgactcactatagggagaccacaacgg (SEQ ID NO: 30) |
| TolAR | ttcagttgccgctttctttc (SEQ ID NO: 31) |
| TolAkR | ccgcacaccagtaaggtgtgcggtttcagttgccgctttctttct (SEQ ID NO: 32) |
| H1Fa | cgcagcctctggtttcaacattAVTRRTWMYKMTatccactgggtccgtcaggc (SEQ ID NO: 33) |
| H1Fb | cgcagcctctggtttcaacattAVTRRTWMYKGGatccactgggtccgtcaggc (SEQ ID NO: 34) |

TABLE 3-continued

Primers for scFv VH library construction

| Primer | Sequence (5' to 3') (SEQ ID NO:) |
|---|---|
| H1Ra | gcctgacggacccagtggatAKMRKWAYYABTaatgttgaaaccagaggctgcg (SEQ ID NO: 35) |
| H1Rb | gcctgacggacccagtggatCCMRKWAYYABTaatgttgaaaccagaggctgcg (SEQ ID NO: 36) |
| H2Fa | gggtaaaggcctggaatgggttGSTDGGattDMTccgDMTRRCggtDMTacgDACtacgccgatagcgtgaaaggc (SEQ ID NO: 37) |
| H2Fb | gggtaaaggcctggaatgggttGSTDHTattDMTccgDMTRRCggtDMTacgDACtacgccgatagcgtgaaaggc (SEQ ID NO: 38) |
| H2Fc | gggtaaaggcctggaatgggttGSTGAAattDMTccgDMTRRCggtDMTacgDACtacgccgatagcgtgaaaggc (SEQ ID NO: 39) |
| H2Ra | gcctttcacgctatcggcgtaGTHcgtAKHaccGYYAKHcggAKHaatCCHASCaacccattccaggccttaccc (SEQ ID NO: 40) |
| H2Rb | gcctttcacgctatcggcgtaGTHcgtAKHaccGYYAKHcggAKHaatADHASCaacccattccaggccttaccc (SEQ ID NO: 41) |
| H2Rc | gcctttcacgctatcggcgtaGTHcgtAKHaccGYYAKHcggAKHaatTTCASCaacccattccaggccttaccc (SEQ ID NO: 42) |
| H3Fa | cggaagataccgccgtttattactgtGCGcgcNNKNNKNNKNNKNNKNNKNNKNNKNNKatggactactgggtcagggcac (SEQ ID NO: 43) |
| H3Fb | cggaagataccgccgtttattactgtGCGcgcNNKNNKNNKNNKNNKNNKNNKNNKKTTTgactactgggtcagggcacc (SEQ ID NO: 44) |
| H3Ra | gtgccctgaccccagtagtccatMNNMNNMNNMNNMNNMNNMNNMNNgcgCGCacagtaataaacggcggtatcttccg (SEQ ID NO: 45) |
| H3Rb | gggtgccctgaccccagtagtcAAAMNNMNNMNNMNNMNNMNNMNNgcgCGCacagtaataaacggcggtatcttccg (SEQ ID NO: 46) |
| VLF | gatatatccatggatattcaaatgacccaatctc (SEQ ID NO: 47) |
| VHR | cgatataaagcttggaactgacggtaacc (SEQ ID NO: 48) |
| VLR | gagattgggtcatttgaatatccatggatatatc (SEQ ID NO: 49) |
| VHF | ggttaccgtcagttccaagctttatatcg (SEQ ID NO: 50) |
| BsaI-VLF | aaaaaggtctcctatggatattcaaatgacccaatctccgtcttc (SEQ ID NO: 51) |
| BsaI-VHR | aaaaaaggtctccccgcggaactgacggtaaccaggtgcc (SEQ ID NO: 52) |

This example demonstrates that the inclusion of GamS protein in the RDRS increases the stability of the mRNA template, and that extracts including GamS protein were successfully used to select for scFv's and Fabs that show specific binding to the target antigen.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

Informal Sequence listing:
Lambda GamS protein sequence
(SEQ ID NO: 1)
MNAYYIQDRLEAQSWARHYQQLAREEKEAELADDMEKGIPQHLFESLCID
HLQRHGASKKSITRAFDDDVEFQERMAEHIRYMVETIAHHQVDIDSEV.

GamSHis gene
(SEQ ID NO: 2)
Atgaacgcttattacattcaggatcgtatgaggctcagagctgggcgcgt
cactaccagcagctcgcccgtgaagagaaagaggcagaactggcagacga
catggaaaaaggggatcccccagcacctgtttgaatcgctatgcatcgatc
atttgcaacgccacggggccagcaaaaaatccattacccgtgcgtttgat
gacgatgttgagtttcaggagcgcatggcagaacacatccggtacatggt
tgaaaccattgctcaccaccaggttgatattgattcagaggtaGGGGGTT
CTCATCATCATCATCATCATTAA GamSHis protein
(SEQ ID NO: 3)
MNAYYIQDRLEAQSWARHYQQLAREEKEAELADDMEKGIPQHLFESLCID
HLQRHGASKKSITRAFDDDVEFQERMAEHIRYMVETIAHHQVDIDSEVGG
SHHHHHH

What is claimed is:

1. A ribosomal display reaction system comprising a mRNA encoding a protein of interest without an operable stop codon, a cell free translation system, and a concentration of λGam protein sufficient to stabilize the mRNA encoding the protein of interest, wherein the λGam protein is the S form and comprises an amino acid sequence having at least 80% sequence identity to SEQ ID NO:1.

2. The system of claim 1, where the λGam protein is present at a concentration of 25-60 μg/ml of extract.

3. The system of claim 1, where the protein of interest is an antibody.

4. The system of claim 1, where the protein of interest is a single chain antibody.

5. The system of claim 1, where the ribosomal display reaction system comprises two or more nucleic acid templates wherein each template encodes a protein of interest having a different primary amino acid sequence from the other templates.

6. A method of stabilizing protein encoding mRNA in a ribosomal display reaction system, the method comprising the step of: combining a nucleic acid template encoding a protein of interest and lacking a operable stop codon with a cell free translation system to yield a ribosomal display reaction system containing a complex of the mRNA encoding the protein of interest, a ribosome and the protein of interest, wherein the system has a concentration of λGam protein sufficient to stabilize the mRNA encoding the protein of interest, wherein the λGam protein is the S form and comprises an amino acid sequence having at least 80% sequence identity to SEQ ID NO:1.

* * * * *